(12) United States Patent
Conway et al.

(10) Patent No.: US 9,248,058 B2
(45) Date of Patent: Feb. 2, 2016

(54) MALE EXTERNAL CATHETER WITH ABSORBENT AND ADHESIVE

(71) Applicant: Rochester Medical Corporation, Stewartville, MN (US)

(72) Inventors: Anthony J. Conway, Chatfield, MN (US); Richard D. Fryer, Jr., Chatfield, MN (US)

(73) Assignee: Rochester Medical Corporation, a subsidiary of C.R. Bard, Inc., Stewartville, MN (US)

( * ) Notice: Subject to any disclaimer, the term of this patent is extended or adjusted under 35 U.S.C. 154(b) by 0 days.

(21) Appl. No.: 14/508,450

(22) Filed: Oct. 7, 2014

(65) Prior Publication Data

US 2015/0025489 A1  Jan. 22, 2015

Related U.S. Application Data

(62) Division of application No. 11/104,388, filed on Apr. 12, 2005, now Pat. No. 8,864,730.

(51) Int. Cl.
*A61F 13/471* (2006.01)
*A61F 13/82* (2006.01)
(Continued)

(52) U.S. Cl.
CPC ............. *A61F 13/471* (2013.01); *A61F 5/451* (2013.01); *A61F 5/453* (2013.01); *A61F 13/82* (2013.01); *A61F 5/4407* (2013.01); *A61F 5/4408* (2013.01); *A61F 6/02* (2013.01); *A61F 6/04* (2013.01); *A61F 2006/044* (2013.01); *A61F 2006/045* (2013.01); *A61F 2006/047* (2013.01); *A61F 2013/15146* (2013.01)

(58) Field of Classification Search
CPC ....... A61F 5/453; A61F 13/471; A61F 13/82; A61F 2006/044; A61F 2013/15146; A61F 6/04; A61F 6/02
See application file for complete search history.

(56) References Cited

U.S. PATENT DOCUMENTS 480,911 A   8/1892  Vance
822,092 A   5/1906  Woodruff
(Continued)

FOREIGN PATENT DOCUMENTS

CA   763930 A    7/1967
DE   1913976 U   4/1965
(Continued)

OTHER PUBLICATIONS

Amirkhalili, Saeid et al., "Mitric Oxide Complexes of Trimethylaluminiurn," Jornal of Organometallic Chemistry, 149 (Jan. 20, 1978) 407-411.
(Continued)

*Primary Examiner* — Adam Marcetich
(74) *Attorney, Agent, or Firm* — Merchant & Gould P.C.

(57) ABSTRACT

The invention relates generally to external urinary catheters for males. More specifically, the invention relates to an external urinary catheter that includes an absorbent material to absorb urinary discharge. The absorbent material can be located in either a distal end of a tubular sheath, or in a receptacle that attached to the distal end of the tubular sheath. The tubular sheath of the external urinary catheter can include a tubular sheath of silicone rubber, wherein the sheath has an inner surface and an outer surface, and a layer of adhesive material directly and non-releasably bonded to the inner surface.

14 Claims, 9 Drawing Sheets

(51) Int. Cl.
*A61F 5/451* (2006.01)
*A61F 5/453* (2006.01)
A61F 6/04 (2006.01)
A61F 6/02 (2006.01)
A61F 5/44 (2006.01)
A61F 13/15 (2006.01)

(56) References Cited

U.S. PATENT DOCUMENTS

| | | |
|---|---|---|
| 1,235,142 A | 7/1917 | Ichilian |
| 1,643,289 A | 9/1927 | Peglay |
| 1,661,494 A | 3/1928 | Nielsen |
| 2,043,630 A | 6/1936 | Raiche |
| 2,213,210 A | 9/1940 | Egbert |
| 2,228,992 A | 1/1941 | Fry |
| 2,230,226 A | 2/1941 | Auzin |
| 2,248,934 A | 7/1941 | Auzin |
| 2,285,502 A | 6/1942 | Dreyfus |
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 3,044,468 A | 7/1962 | Birtwell |
| 3,053,257 A | 9/1962 | Birtwell |
| 3,076,464 A | 2/1963 | Rosenberg |
| 3,154,080 A | 10/1964 | Rowan et al. |
| 3,169,527 A | 2/1965 | Sheridan |
| 3,211,151 A | 10/1965 | Foderick et al. |
| 3,304,353 A | 2/1967 | Harautuneian |
| 3,345,988 A | 10/1967 | Vitello |
| 3,394,704 A | 7/1968 | Den |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,503,400 A | 3/1970 | Osthagen |
| 3,508,959 A | 4/1970 | Krahnke |
| 3,509,884 A | 5/1970 | Bell |
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,683,928 A | 8/1972 | Kuntz |
| 3,695,921 A | 10/1972 | Shepard et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,838,728 A | 10/1974 | Voegele |
| 3,841,304 A | 10/1974 | Jones |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,903,893 A | 9/1975 | Scheer |
| 3,924,634 A | 12/1975 | Taylor et al. |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,055,682 A | 10/1977 | Merrill |
| 4,062,363 A | 12/1977 | Bonner, Jr. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch et al. |
| 4,266,999 A | 5/1981 | Baier |
| 4,269,310 A | 5/1981 | Uson et al. |
| 4,284,459 A | 8/1981 | Patel et al. |
| 4,287,227 A | 9/1981 | Kamada et al. |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,342,392 A | 8/1982 | Cox |
| 4,343,788 A | 8/1982 | Mustacich et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,446,860 A | 5/1984 | Gutnick |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,515,593 A | 5/1985 | Norton |
| 4,534,768 A | 8/1985 | Osburn et al. |
| 4,539,234 A | 9/1985 | Sakamoto et al. |
| 4,540,409 A | 9/1985 | Nystrom et al. |
| 4,553,533 A | 11/1985 | Leighton |
| 4,563,184 A | 1/1986 | Korol |

(56) References Cited

U.S. PATENT DOCUMENTS

| | | |
|---|---|---|
| 4,568,340 A | 2/1986 | Giacalone |
| 4,571,239 A | 2/1986 | Heyman |
| 4,571,240 A | 2/1986 | Samson et al. |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,586,974 A | 5/1986 | Nystrom et al. |
| 4,589,874 A | 5/1986 | Riedel et al. |
| 4,592,920 A | 6/1986 | Murtfeldt |
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,610,685 A * | 9/1986 | Raley .......................... 604/366 |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,633,863 A | 1/1987 | Filips et al. |
| 4,634,433 A | 1/1987 | Osborne |
| 4,637,907 A | 1/1987 | Hegel et al. |
| 4,638,790 A | 1/1987 | Conway et al. |
| 4,640,668 A | 2/1987 | Yang |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,699,616 A | 10/1987 | Nowak et al. |
| 4,710,169 A | 12/1987 | Christopher |
| 4,710,181 A | 12/1987 | Fuqua |
| 4,731,064 A | 3/1988 | Heyden |
| 4,737,219 A | 4/1988 | Taller et al. |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,768,503 A | 9/1988 | Highgate et al. |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,448 A * | 9/1989 | Berg .......................... 604/349 |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| 4,919,966 A | 4/1990 | Shlenker |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,952,618 A | 8/1990 | Olsen |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,059,190 A | 10/1991 | Novak |
| 5,071,406 A | 12/1991 | Jang |
| 5,078,707 A | 1/1992 | Peter Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,176,666 A | 1/1993 | Conway et al. |
| 5,197,957 A | 3/1993 | Wendler |
| 5,201,724 A | 4/1993 | Hukins et al. |
| 5,209,726 A | 5/1993 | Goosen |
| 5,211,640 A | 5/1993 | Wendler |
| 5,226,530 A | 7/1993 | Golden |
| 5,234,411 A | 8/1993 | Vaillancourt |
| 5,236,422 A | 8/1993 | Eplett, Jr. |
| 5,242,391 A | 9/1993 | Place et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,279,600 A | 1/1994 | Hogan |
| 5,290,306 A | 3/1994 | Trotta et al. |
| 5,300,052 A | 4/1994 | Kubo |
| 5,306,226 A | 4/1994 | Salama |
| 5,334,175 A | 8/1994 | Conway et al. |
| 5,335,775 A | 8/1994 | Scanlon et al. |
| 5,336,211 A | 8/1994 | Metz |
| 5,346,483 A | 9/1994 | Thaxton, Sr. |
| 5,348,536 A | 9/1994 | Young et al. |
| 5,352,182 A | 10/1994 | Kalb et al. |
| 5,360,402 A | 11/1994 | Conway et al. |

(56) References Cited

U.S. PATENT DOCUMENTS

| | | |
|---|---|---|
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,402,886 A | 4/1995 | McGlinch |
| 5,409,495 A | 4/1995 | Osborn |
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,447,231 A | 9/1995 | Kastenhofer |
| 5,451,424 A | 9/1995 | Solomon et al. |
| 5,454,798 A | 10/1995 | Kubalak et al. |
| 5,464,650 A | 11/1995 | Berg et al. |
| 5,479,945 A | 1/1996 | Simon |
| 5,482,740 A | 1/1996 | Conway et al. |
| 5,483,976 A | 1/1996 | McLaughlin et al. |
| 5,501,669 A | 3/1996 | Conway et al. |
| 5,509,427 A | 4/1996 | Simon et al. |
| 5,513,659 A | 5/1996 | Buuck et al. |
| 5,513,660 A | 5/1996 | Simon et al. |
| 5,531,715 A | 7/1996 | Engelson et al. |
| 5,531,717 A | 7/1996 | Roberto et al. |
| 5,538,584 A | 7/1996 | Metz |
| 5,549,924 A | 8/1996 | Shlenker et al. |
| 5,554,141 A | 9/1996 | Wendler |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,593,718 A | 1/1997 | Conway et al. |
| 5,599,321 A | 2/1997 | Conway et al. |
| 5,614,143 A | 3/1997 | Hager |
| 5,622,711 A | 4/1997 | Chen |
| 5,624,395 A | 4/1997 | Mikhail et al. |
| 5,630,429 A | 5/1997 | Dann |
| 5,633,010 A | 5/1997 | Chen |
| 5,643,235 A | 7/1997 | Figuerido |
| 5,670,111 A | 9/1997 | Conway et al. |
| 5,670,557 A | 9/1997 | Dietz et al. |
| 5,671,755 A | 9/1997 | Simon et al. |
| 5,674,561 A | 10/1997 | Dietz et al. |
| 5,679,399 A | 10/1997 | Shlenker et al. |
| 5,695,485 A | 12/1997 | Duperret et al. |
| 5,702,381 A | 12/1997 | Cottenden |
| 5,707,357 A | 1/1998 | Mikhail et al. |
| 5,709,672 A | 1/1998 | Illner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,752,525 A | 5/1998 | Simon et al. |
| 5,756,144 A | 5/1998 | Wolff et al. |
| 5,762,996 A | 6/1998 | Lucas et al. |
| 5,779,632 A | 7/1998 | Dietz et al. |
| 5,779,670 A | 7/1998 | Bidwell et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,806,527 A | 9/1998 | Borodulin et al. |
| 5,810,789 A | 9/1998 | Powers et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,853,518 A | 12/1998 | Utas et al. |
| 5,853,750 A | 12/1998 | Dietz et al. |
| 5,877,243 A | 3/1999 | Sarangapani |
| 5,895,374 A | 4/1999 | Rodsten et al. |
| 5,897,535 A | 4/1999 | Feliziani et al. |
| 5,902,631 A | 5/1999 | Wang et al. |
| 5,906,575 A | 5/1999 | Conway et al. |
| 5,931,303 A | 8/1999 | Salvadori |
| 5,931,304 A | 8/1999 | Hammond |
| 5,971,954 A | 10/1999 | Conway et al. |
| 5,980,483 A | 11/1999 | Dimitri et al. |
| 5,980,507 A | 11/1999 | Fassuliotis et al. |
| 6,004,305 A | 12/1999 | Hursman et al. |
| 6,007,524 A | 12/1999 | Schneider |
| 6,007,526 A | 12/1999 | Passalaqua et al. |
| 6,050,934 A | 4/2000 | Mikhail et al. |
| 6,053,905 A | 4/2000 | Daignault, Jr. et al. |
| 6,059,107 A | 5/2000 | Nosted et al. |
| 6,063,063 A | 5/2000 | Harboe et al. |
| 6,065,597 A | 5/2000 | Pettersson et al. |
| 6,090,075 A | 7/2000 | House |
| 6,098,625 A | 8/2000 | Winkler |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,186,990 B1 | 2/2001 | Chen et al. |
| 6,206,885 B1 | 3/2001 | Ghahremani et al. |
| 6,231,501 B1 | 5/2001 | Ditter |
| 6,248,096 B1 * | 6/2001 | Dwork et al. ................. 604/349 |
| 6,254,570 B1 | 7/2001 | Rutner et al. |
| 6,261,255 B1 | 7/2001 | Mullis et al. |
| 6,261,271 B1 | 7/2001 | Solomon et al. |
| 6,280,425 B1 | 8/2001 | Del Guercio |
| 6,296,627 B1 | 10/2001 | Edwards |
| 6,299,598 B1 | 10/2001 | Bander |
| 6,315,711 B1 | 11/2001 | Conway et al. |
| 6,326,421 B1 | 12/2001 | Lipman |
| 6,338,729 B1 * | 1/2002 | Wada et al. ............... 604/385.09 |
| 6,355,004 B1 | 3/2002 | Pedersen et al. |
| 6,379,334 B1 | 4/2002 | Frassica |
| 6,383,434 B2 | 5/2002 | Conway et al. |
| 6,387,080 B1 | 5/2002 | Rødsten |
| 6,391,010 B1 | 5/2002 | Wilcox |
| 6,402,726 B1 | 6/2002 | Genese |
| 6,409,717 B1 | 6/2002 | Israelsson et al. |
| 6,437,038 B1 | 8/2002 | Chen |
| 6,440,060 B1 | 8/2002 | Latour, Jr. |
| 6,468,245 B2 | 10/2002 | Alexandersen et al. |
| 6,479,000 B2 | 11/2002 | Conway et al. |
| 6,479,726 B1 | 11/2002 | Cole |
| 6,509,319 B1 | 1/2003 | Raad et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,626,888 B1 | 9/2003 | Conway et al. |
| 6,632,204 B2 | 10/2003 | Guldfeldt et al. |
| 6,634,498 B2 | 10/2003 | Kayerod et al. |
| 6,638,269 B2 | 10/2003 | Wilcox |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,716,895 B1 | 4/2004 | Terry |
| 6,719,709 B2 | 4/2004 | Whalen et al. |
| 6,723,350 B2 | 4/2004 | Burrell et al. |
| 6,733,474 B2 | 5/2004 | Kusleika |
| 6,736,805 B2 | 5/2004 | Israelsson et al. |
| 6,740,273 B2 | 5/2004 | Lee |
| 6,767,551 B2 | 7/2004 | McGhee et al. |
| D496,266 S | 9/2004 | Nestenborg et al. |
| 6,787,156 B1 | 9/2004 | Bar-Shalom |
| 6,797,743 B2 | 9/2004 | McDonald et al. |
| 6,803,420 B2 | 10/2004 | Cleary et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |

(56) References Cited

U.S. PATENT DOCUMENTS

| | | |
|---|---|---|
| 6,869,416 B2 | 3/2005 | Windheuser et al. |
| 6,872,195 B2 | 3/2005 | Modak et al. |
| 6,887,230 B2 | 5/2005 | Kubalak et al. |
| 6,939,339 B1 | 9/2005 | Axexandersen et al. |
| 6,939,554 B2 | 9/2005 | McDonald et al. |
| 6,949,090 B1 | 9/2005 | Leers et al. |
| 6,951,902 B2 | 10/2005 | McDonald et al. |
| 7,001,370 B2 | 2/2006 | Kubalak et al. |
| 7,033,367 B2 | 4/2006 | Ghahremani et al. |
| 7,066,912 B2 | 6/2006 | Nestenborg et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,204,940 B2 | 4/2007 | McDonald et al. |
| 7,211,275 B2 | 5/2007 | Ying et al |
| 7,294,117 B2 | 11/2007 | Provost-tine et al. |
| 7,311,698 B2 | 12/2007 | Tanghoj et al. |
| 7,329,412 B2 | 2/2008 | Modak et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,381,768 B2 | 6/2008 | Wiercinski et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,691,476 B2 | 4/2010 | Finley |
| 7,717,902 B2 | 5/2010 | Sauer |
| 7,749,529 B2 | 7/2010 | Ash et al. |
| 7,767,291 B2 | 8/2010 | Taylor |
| 7,770,726 B2 | 8/2010 | Murray et al. |
| 7,770,728 B2 | 8/2010 | Kærn |
| 7,780,642 B2 | 8/2010 | Rasmussen et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,052,673 B2 | 11/2011 | Nestenborg |
| 8,058,341 B2 | 11/2011 | Tosaki et al. |
| 8,066,693 B2 | 11/2011 | Tanghoj et al. |
| 8,127,922 B2 | 3/2012 | Nordholm et al. |
| 8,163,327 B2 | 4/2012 | Finley |
| 8,177,774 B2 | 5/2012 | House |
| 8,181,778 B1 | 5/2012 | Van Groningen et al. |
| 8,192,413 B2 | 6/2012 | Bjerregaard |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,298,202 B2 | 10/2012 | McCray |
| 8,303,556 B2 | 11/2012 | White |
| 8,328,792 B2 | 12/2012 | Nishtala et al. |
| 8,356,457 B2 | 1/2013 | Murray et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 2001/0001443 A1 | 5/2001 | Kayerod et al. |
| 2001/0031933 A1 | 10/2001 | Cannon |
| 2001/0054562 A1 | 12/2001 | Pettersson et al. |
| 2002/0013564 A1 | 1/2002 | Kubalek et al. |
| 2002/0032406 A1 | 3/2002 | Kusleika |
| 2002/0103467 A1 | 8/2002 | Kubalak |
| 2002/0147265 A1 | 10/2002 | Ding et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018321 A1 | 1/2003 | Rosenblum |
| 2003/0018322 A1 | 1/2003 | Tanghoj et al. |
| 2003/0055403 A1 | 3/2003 | Nestenborg et al. |
| 2003/0060807 A1 | 3/2003 | Tanghoj et al. |
| 2003/0083644 A1 | 5/2003 | Avaltroni |
| 2003/0114823 A1 | 6/2003 | Bosselaar et al. |
| 2003/0130646 A1 | 7/2003 | Kubalak et al. |
| 2003/0168365 A1 | 9/2003 | Kaern |
| 2004/0030301 A1 | 2/2004 | Hunter |
| 2004/0055925 A1 | 3/2004 | Franks-Farah et al. |
| 2004/0074794 A1 | 4/2004 | Conway et al. |
| 2004/0097892 A1 | 5/2004 | Evans et al. |
| 2004/0133156 A1 | 7/2004 | Diaz et al. |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0043715 A1 | 2/2005 | Nestenborg et al. |
| 2005/0049577 A1 | 3/2005 | Snell et al. |
| 2005/0070882 A1 | 3/2005 | McBride |
| 2005/0080399 A1 | 4/2005 | Bolmsjo et al. |
| 2005/0096688 A1 | 5/2005 | Slazas et al. |
| 2005/0101924 A1 | 5/2005 | Elson et al. |
| 2005/0109648 A1 | 5/2005 | Kerzman et al. |
| 2005/0137582 A1 | 6/2005 | Kull-Osterlin et al. |
| 2005/0148950 A1 | 7/2005 | Windheuser et al. |
| 2005/0177104 A1 | 8/2005 | Conway |
| 2005/0199521 A1 | 9/2005 | Givens |
| 2005/0214443 A1 | 9/2005 | Madsen |
| 2005/0282977 A1 | 12/2005 | Stempel et al. |
| 2005/0283136 A1 | 12/2005 | Skarda |
| 2006/0004332 A1 | 1/2006 | Marx |
| 2006/0025753 A1 | 2/2006 | Kubalak et al. |
| 2006/0041246 A1 | 2/2006 | Provost-tine et al. |
| 2006/0058777 A1 | 3/2006 | Nielsen |
| 2006/0163097 A1 | 7/2006 | Murray et al. |
| 2006/0196783 A1 | 9/2006 | Bruun et al. |
| 2006/0206070 A1* | 9/2006 | Larsen ............ 604/354 |
| 2006/0229576 A1 | 10/2006 | Conway et al. |
| 2006/0240069 A1 | 10/2006 | Utas et al. |
| 2007/0016168 A1 | 1/2007 | Conway |
| 2007/0088330 A1 | 4/2007 | House |
| 2007/0161971 A1 | 7/2007 | House |
| 2008/0015527 A1 | 1/2008 | House |
| 2008/0091145 A1 | 4/2008 | House |
| 2008/0103464 A1 | 5/2008 | Mosler et al. |
| 2008/0172040 A1 | 7/2008 | Smith |
| 2008/0172042 A1 | 7/2008 | House |
| 2008/0179208 A1 | 7/2008 | Murray et al. |
| 2008/0183262 A1 | 7/2008 | Dowling |
| 2008/0215021 A1 | 9/2008 | Cisko, Jr. et al. |
| 2008/0243081 A1 | 10/2008 | Nance et al. |
| 2008/0279907 A1 | 11/2008 | Ash et al. |
| 2009/0000970 A1 | 1/2009 | Bordeau et al. |
| 2009/0005725 A1 | 1/2009 | Shorey |

(56) References Cited

U.S. PATENT DOCUMENTS

| | | |
|---|---|---|
| 2009/0043287 A1 | 2/2009 | Mosler et al. |
| 2009/0048570 A1 | 2/2009 | Jensen |
| 2009/0101531 A1 | 4/2009 | Nordholm et al. |
| 2009/0131917 A1 | 5/2009 | Kavanagh et al. |
| 2009/0163884 A1 | 6/2009 | Kull-Osterlin et al. |
| 2009/0200187 A1 | 8/2009 | Nestenborg et al. |
| 2009/0221992 A1 | 9/2009 | Hannon et al. |
| 2009/0234294 A1 | 9/2009 | Harvey et al. |
| 2009/0240214 A1 | 9/2009 | Conway et al. |
| 2010/0010086 A1 | 1/2010 | Ash et al. |
| 2010/0025273 A1 | 2/2010 | Matsuda et al. |
| 2010/0030197 A1 | 2/2010 | House |
| 2010/0036363 A1 | 2/2010 | Watanabe et al. |
| 2010/0133172 A1 | 6/2010 | Song et al. |
| 2010/0155268 A1 | 6/2010 | Murray et al. |
| 2010/0200002 A1 | 8/2010 | Orban, III et al. |
| 2010/0240750 A1 | 9/2010 | Ash et al. |
| 2010/0256576 A1 | 10/2010 | Aggarwal et al. |
| 2010/0322996 A1 | 12/2010 | Wibaux et al. |
| 2011/0056852 A1 | 3/2011 | Frojd |
| 2011/0100526 A1 | 5/2011 | Umebayashi |
| 2011/0114520 A1 | 5/2011 | Matthison-Hansen |
| 2011/0118670 A1 | 5/2011 | Kay et al. |
| 2011/0137296 A1 | 6/2011 | Tanghoj |
| 2011/0152843 A1 | 6/2011 | Wedlin et al. |
| 2011/0178507 A1 | 7/2011 | Bracken et al. |
| 2011/0184386 A1 | 7/2011 | House |
| 2011/0213025 A1 | 9/2011 | Finch, Jr. |
| 2011/0284409 A1 | 11/2011 | Murray et al. |
| 2012/0029451 A1 | 2/2012 | Conway |
| 2012/0179144 A1 | 7/2012 | Carleo |
| 2012/0203182 A1 | 8/2012 | Kay et al. |
| 2012/0228165 A1 | 9/2012 | Murray et al. |
| 2012/0271101 A1 | 10/2012 | Tan |
| 2012/0316515 A1 | 12/2012 | Terry |
| 2013/0006226 A1 | 1/2013 | Hong et al. |
| 2013/0037306 A1 | 2/2013 | Kim |
| 2013/0131647 A1 | 5/2013 | Nielsen |
| 2013/0138083 A1 | 5/2013 | Tennican |
| 2013/0138088 A1 | 5/2013 | Nielsen |
| 2013/0153446 A1 | 6/2013 | Utas et al. |
| 2014/0142554 A1 | 5/2014 | Conway et al. |
| 2014/0142555 A1 | 5/2014 | Conway et al. |

FOREIGN PATENT DOCUMENTS

| | | |
|---|---|---|
| DE | 19826746 C1 | 11/1999 |
| EP | 0055023 A2 | 6/1982 |
| EP | 0182409 A1 | 5/1986 |
| EP | 0184629 A2 | 6/1986 |
| EP | 0187846 A1 | 7/1986 |
| EP | 0193406 A2 | 9/1986 |
| EP | 0217771 | 4/1987 |
| EP | 0218203 A1 | 4/1987 |
| EP | 0236458 A1 | 9/1987 |
| EP | 0252918 A1 | 1/1988 |
| EP | 0298634 A1 | 1/1989 |
| EP | 0303487 A2 | 2/1989 |
| EP | 0335564 A1 | 10/1989 |
| EP | 0352043 A1 | 1/1990 |
| EP | 0390720 A1 | 10/1990 |
| EP | 0407218 A1 | 1/1991 |
| EP | 0471553 A1 | 2/1992 |
| EP | 0479935 A1 | 4/1992 |
| EP | 0528965 A1 | 3/1993 |
| EP | 0553960 A1 | 8/1993 |
| EP | 0590104 A1 | 4/1994 |
| EP | 0598191 A1 | 5/1994 |
| EP | 0663196 A1 | 7/1995 |
| EP | 0677299 | 10/1995 |
| EP | 0680895 A1 | 11/1995 |
| EP | 0685179 A1 | 12/1995 |
| EP | 0699086 A1 | 3/1996 |
| EP | 0767639 A1 | 4/1997 |
| EP | 0768069 A1 | 4/1997 |
| EP | 0815037 A1 | 1/1998 |
| EP | 0909249 A1 | 4/1999 |
| EP | 0923398 | 6/1999 |
| EP | 0935478 A1 | 8/1999 |
| EP | 0959930 | 12/1999 |
| EP | 0977610 A2 | 2/2000 |
| EP | 1023882 | 8/2000 |
| EP | 1047360 A1 | 11/2000 |
| EP | 1090656 | 4/2001 |
| EP | 1115450 A1 | 7/2001 |
| EP | 1131022 A1 | 9/2001 |
| EP | 1145729 | 10/2001 |
| EP | 1245205 | 10/2002 |
| EP | 1308146 | 5/2003 |
| EP | 1347723 A1 | 10/2003 |
| EP | 1406690 A2 | 4/2004 |
| EP | 1427467 A2 | 6/2004 |
| EP | 1485158 A2 | 12/2004 |
| EP | 1498151 | 1/2005 |
| EP | 1578308 A1 | 9/2005 |
| EP | 1606196 A2 | 12/2005 |
| EP | 1615690 A1 | 1/2006 |
| EP | 1629799 A1 | 3/2006 |
| EP | 1641510 A1 | 4/2006 |
| EP | 1642610 | 4/2006 |
| EP | 1642611 | 4/2006 |
| EP | 1647298 A2 | 4/2006 |
| EP | 1786501 A2 | 5/2007 |
| EP | 1788990 A1 | 5/2007 |
| EP | 1793938 A1 | 6/2007 |
| EP | 1799163 A1 | 6/2007 |
| EP | 1904003 A2 | 4/2008 |
| EP | 1948279 A1 | 7/2008 |
| EP | 1955683 A1 | 8/2008 |
| EP | 2216064 A1 | 8/2010 |
| EP | 2226041 A2 | 9/2010 |
| EP | 2226042 A2 | 9/2010 |
| EP | 2258435 A1 | 12/2010 |
| EP | 2275058 A1 | 1/2011 |
| EP | 2292293 A1 | 3/2011 |
| EP | 2292294 A1 | 3/2011 |
| EP | 2423125 A1 | 2/2012 |
| EP | 2423126 A1 | 2/2012 |
| EP | 2423127 A1 | 2/2012 |
| EP | 2450076 A1 | 5/2012 |
| EP | 2468347 A1 | 6/2012 |
| FR | 1558162 A | 2/1969 |
| FR | 2794638 A | 12/2000 |
| FR | 2855399 A1 | 12/2004 |
| GB | 322426 A | 12/1929 |
| GB | 1131865 A | 10/1968 |
| GB | 2150938 A | 7/1985 |
| GB | 2187670 A | 9/1987 |
| WO | 8401102 A1 | 3/1984 |
| WO | 8600816 A1 | 2/1986 |
| WO | 8606284 | 11/1986 |
| WO | 8701582 A1 | 3/1987 |
| WO | 8909626 A1 | 10/1989 |
| WO | 9004431 A1 | 5/1990 |
| WO | 9110466 A1 | 7/1991 |
| WO | 9110467 A1 | 7/1991 |
| WO | 9117728 A1 | 11/1991 |
| WO | 9208426 A1 | 5/1992 |
| WO | 9210220 A1 | 6/1992 |
| WO | 9211826 A1 | 7/1992 |
| WO | 9219192 A1 | 11/1992 |
| WO | 9300054 A1 | 1/1993 |
| WO | 9331821 A1 | 6/1993 |
| WO | 9314806 A1 | 8/1993 |
| WO | 9406377 A1 | 3/1994 |
| WO | 9416747 A1 | 8/1994 |
| WO | 9426215 A1 | 11/1994 |
| WO | 9508968 A1 | 4/1995 |
| WO | 9509667 A1 | 4/1995 |
| WO | 9517862 A1 | 7/1995 |
| WO | 9534253 A1 | 12/1995 |
| WO | 9600541 A1 | 1/1996 |
| WO | 9604119 A1 | 2/1996 |

(56) References Cited

FOREIGN PATENT DOCUMENTS

| | | |
|---|---|---|
| WO | 9619254 A1 | 6/1996 |
| WO | 9626688 A1 | 9/1996 |
| WO | 9630277 A1 | 10/1996 |
| WO | 9634587 A1 | 11/1996 |
| WO | 9638192 A1 | 12/1996 |
| WO | 9639096 A1 | 12/1996 |
| WO | 9725947 A1 | 7/1997 |
| WO | 9726937 | 7/1997 |
| WO | 9741811 | 11/1997 |
| WO | 9806642 A1 | 2/1998 |
| WO | 9907313 A1 | 2/1999 |
| WO | 9930761 A1 | 6/1999 |
| WO | 9936009 A1 | 7/1999 |
| WO | 0025848 A2 | 5/2000 |
| WO | 0030575 A1 | 6/2000 |
| WO | 0047494 | 8/2000 |
| WO | 0143807 | 6/2001 |
| WO | 0152763 | 7/2001 |
| WO | 0193935 | 12/2001 |
| WO | 0236192 | 5/2002 |
| WO | 02053070 A1 | 7/2002 |
| WO | 02060361 A2 | 8/2002 |
| WO | 03002178 | 1/2003 |
| WO | 03008029 A2 | 1/2003 |
| WO | 03022333 A1 | 3/2003 |
| WO | 03064279 A1 | 8/2003 |
| WO | 03092779 | 11/2003 |
| WO | 2004004611 A1 | 1/2004 |
| WO | 2004004796 A1 | 1/2004 |
| WO | 2004030722 | 4/2004 |
| WO | 2004032992 A2 | 4/2004 |
| WO | 2004045696 | 6/2004 |
| WO | 2004050155 | 6/2004 |
| WO | 2004052440 | 6/2004 |
| WO | 2004056290 A1 | 7/2004 |
| WO | 2004056414 | 7/2004 |
| WO | 2004056909 A1 | 7/2004 |
| WO | 2004075944 | 9/2004 |
| WO | 2004089454 | 10/2004 |
| WO | 2005004964 | 1/2005 |
| WO | 2005014055 A2 | 2/2005 |
| WO | 2005061035 | 7/2005 |
| WO | 2005092418 | 10/2005 |
| WO | 2006005349 A2 | 1/2006 |
| WO | 2006009509 A1 | 1/2006 |
| WO | 2006009596 A1 | 1/2006 |
| WO | 2006017439 A2 | 2/2006 |
| WO | 2006021590 A1 | 3/2006 |
| WO | 2006027349 A1 | 3/2006 |
| WO | 2006097109 A2 | 9/2006 |
| WO | 2006110695 A2 | 10/2006 |
| WO | 2006112782 A1 | 10/2006 |
| WO | 2006130776 A2 | 12/2006 |
| WO | 2007001526 A2 | 1/2007 |
| WO | 2007038988 A1 | 4/2007 |
| WO | 2007083033 A2 | 7/2007 |
| WO | 2008089770 A1 | 7/2008 |
| WO | 2008104603 A1 | 9/2008 |
| WO | 2008138351 A1 | 11/2008 |
| WO | 2008138352 A1 | 11/2008 |
| WO | 2009000277 A1 | 12/2008 |
| WO | 2009043872 A1 | 4/2009 |
| WO | 2009068043 A2 | 6/2009 |
| WO | 2009080265 A1 | 7/2009 |
| WO | 2009108243 A1 | 9/2009 |
| WO | 2010006620 A1 | 1/2010 |
| WO | 2010054659 A1 | 5/2010 |
| WO | 2010054666 A1 | 5/2010 |
| WO | 2010129362 A1 | 11/2010 |
| WO | 2010130261 A1 | 11/2010 |
| WO | 2010149174 A1 | 12/2010 |
| WO | 2010149175 A1 | 12/2010 |
| WO | 2010151682 A2 | 12/2010 |
| WO | 2011011023 A1 | 1/2011 |
| WO | 2011014201 A1 | 2/2011 |
| WO | 2011019359 A1 | 2/2011 |
| WO | 2011026929 A1 | 3/2011 |
| WO | 2011026930 A1 | 3/2011 |
| WO | 2011063816 A1 | 6/2011 |
| WO | 2011073403 A1 | 6/2011 |
| WO | 2011076211 A1 | 6/2011 |
| WO | 2011079129 A1 | 6/2011 |
| WO | 2011109393 A1 | 9/2011 |
| WO | 2012016570 A2 | 2/2012 |
| WO | 2012016571 A2 | 2/2012 |
| WO | 2012018402 A1 | 2/2012 |
| WO | 2012079590 A1 | 6/2012 |
| WO | 2012134804 A1 | 10/2012 |
| WO | 2013010745 A1 | 1/2013 |
| WO | 2013029621 A1 | 3/2013 |
| WO | 2014081853 A1 | 5/2014 |
| WO | 2014081859 A1 | 5/2014 |

OTHER PUBLICATIONS

Angus Chemie GmbH Technical Data Sheet for AMP-95 dated Mar. 6, 2006.
EP 12159487.3 filed Mar. 14, 2012 Exam Report dated Jul. 31, 2014.
Ethomeen C/25 Information Sheet dated Jul. 28, 2005.
Johnson, James et al., "Activities of a Nitrofurazone-Containing Urinary Catheter and a Silver Hydrogel Catheter against Multidrug-Resistant Bacteria Characteristic of Catheter-Associated Urinary Tract Infection," Antimicrobial Agents and Chemotherapy, col. 43, No. 12, Dec. 1999, pp. 2990-2995.
Lubrizol Technical Data Sheet, Neutralizing Carbopol®* and Pemulen™ Polymers in Aqueous and Hydroalcoholic Systems, Sep. 16, 2009.
Newman, Diane et al., "Review of Intermittent Catheterization and Current Best Practices," Urol Nurs. 2011:31(1).
PCT/US13/71046 filed Nov. 20, 2013 International Search Report and Written Opinion dated Feb. 21, 2014.
PCT/US13/71060 filed Nov. 20, 2013 International Search Report and Written Opinion dated Jan. 30, 2014.
U.S. Appl. No. 11/104,388, filed Apr. 12, 2005 Notice of Allowance dated Mar. 21, 2014.
U.S. Appl. No. 13/047,175, filed Mar. 14, 2011 Final Office Action dated Mar. 17, 2014.
U.S. Appl. No. 13/682,406, filed Nov. 20, 2012 Non-Final Office Action dated Apr. 21, 2014.
U.S. Appl. No. 13/682,420, filed Nov. 20, 2012 Final Office Action dated Jul. 15, 2014.
U.S. Appl. No. 13/682,420, filed Nov. 20, 2012 Non-Final Office Action dated Apr. 2, 2014.
U.S. Appl. No. 13/705,695, filed Dec. 5, 2012 Non-Final Office Action dated Aug. 26, 2014.
Vapro Product Brochure, 2009.

* cited by examiner

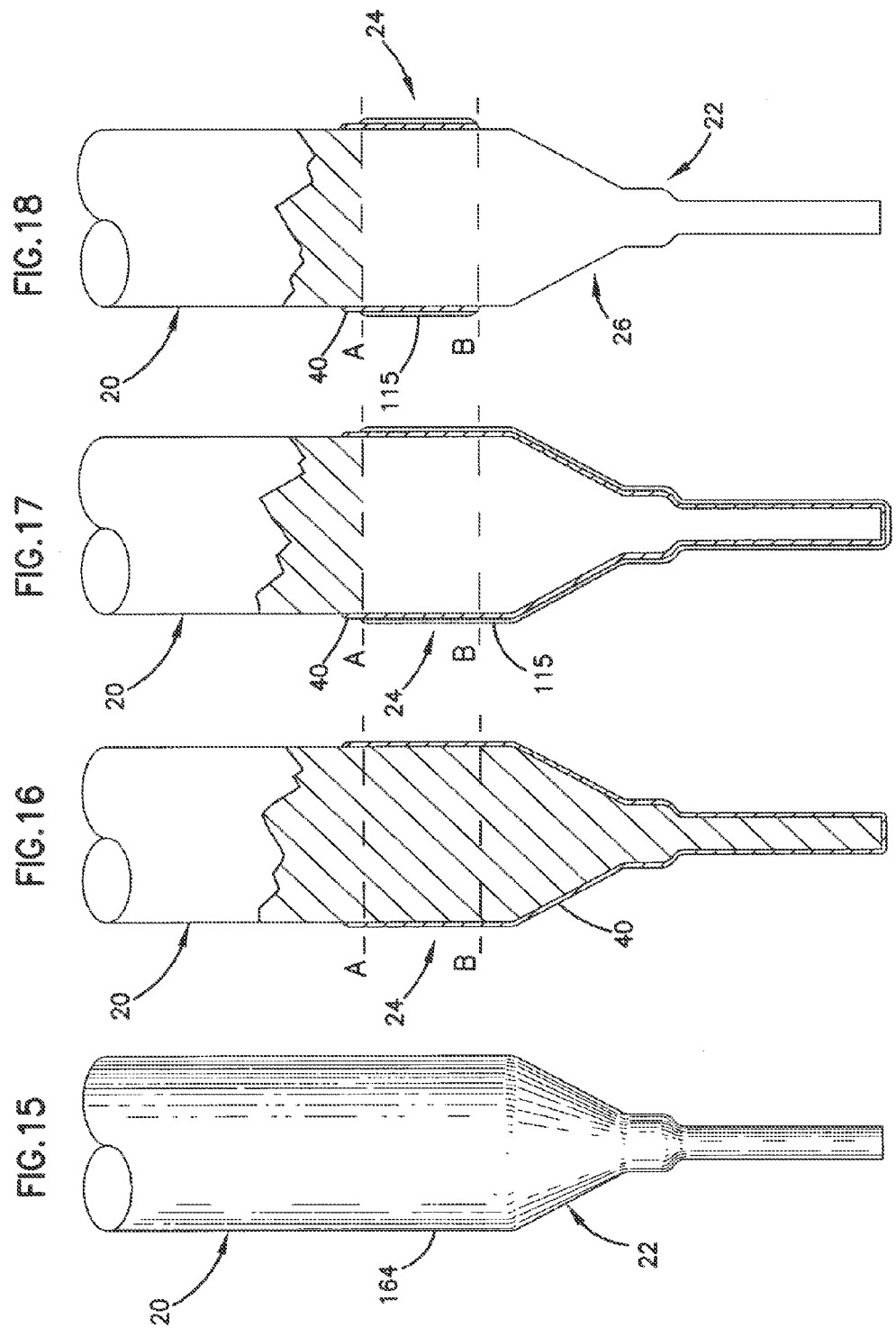

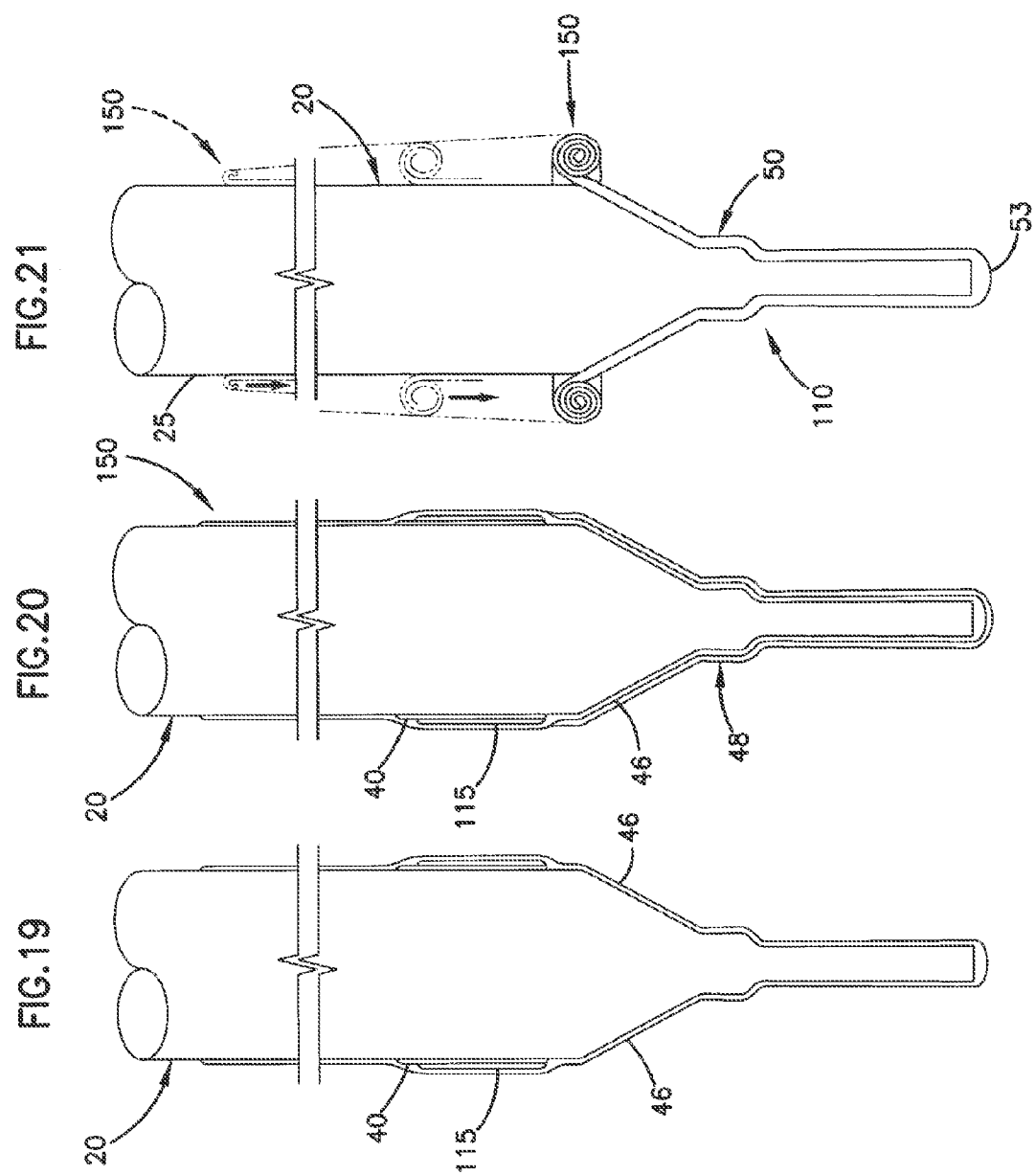

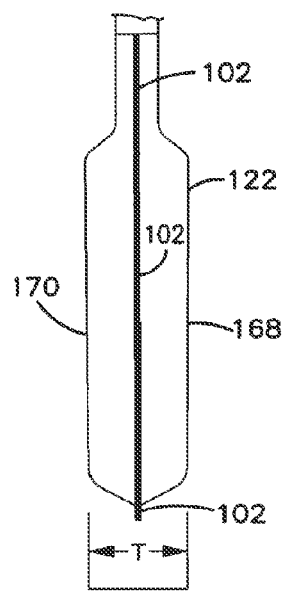
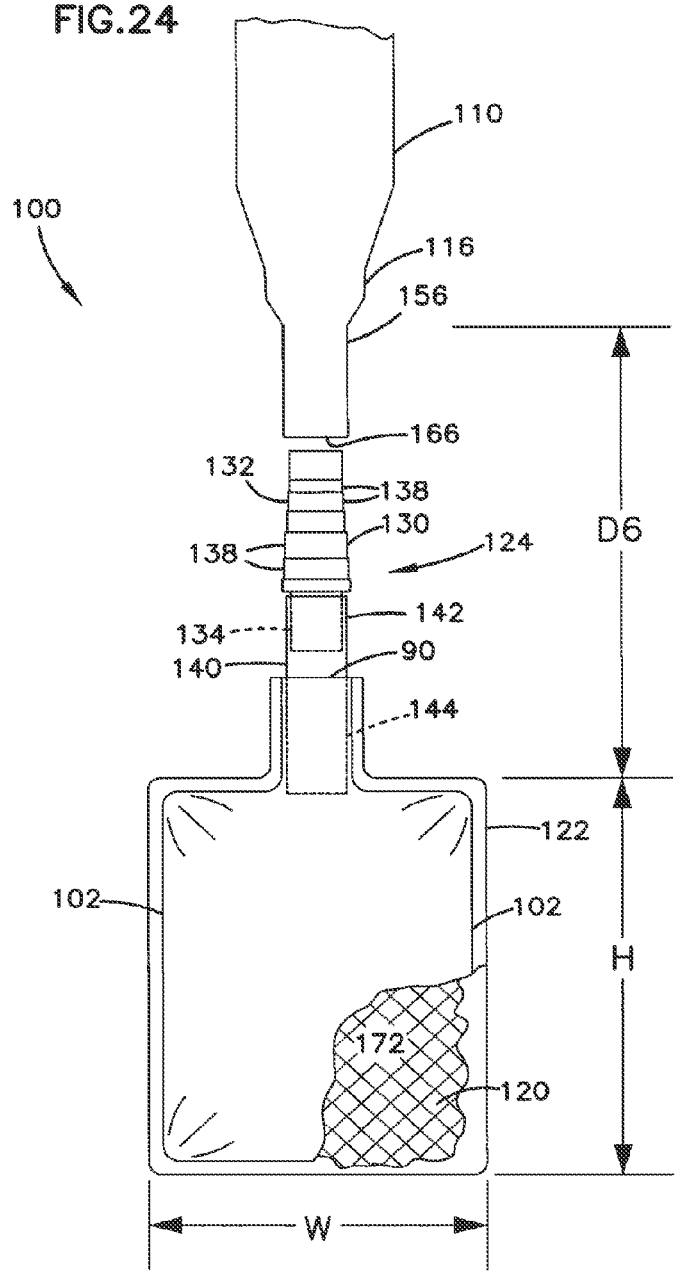

MALE EXTERNAL CATHETER WITH ABSORBENT AND ADHESIVE

PRIORITY

This application is a division of U.S. patent application Ser. No. 11/104,388, filed Apr. 12, 2005, now U.S. Pat. No. 8,864, 730, which is incorporated by reference in its entirety into this application.

TECHNICAL FIELD

The invention relates generally to external urinary catheters for males. More specifically, the invention relates to an external urinary catheter that includes an absorbent material to absorb urinary discharge.

BACKGROUND

Urinary incontinence can be a serious problem for men. Many incontinent men, particularly post prostatectomy patients, leak only small amounts of urine between normal voiding. Generally, male incontinence is handled through use of urine collection devices or absorbent pads. Urine collection devices include what is commonly called a "leg bag." A leg bag generally includes a tube and a large collection bag sized to collect an amount of urine typically discharged during voiding. The tube is retained near the urethra and extends to a location where the large collection bag resides. Often the large collection bag is strapped to the user's leg; hence the term "leg bag."

Existing remedies, although suited for individuals who leak a substantial volume of urine, are not well suited for an incontinent male that leaks only small volumes of urine between voiding. The existing devices are big, bulky, and uncomfortable. Other existing devices occlude leakage of urine, and are also uncomfortable. Some men will forego wearing such devices even though they suffer from urinary incontinence. Such men, and others using existing devices for the collection of only small amounts of urine, would benefit from a smaller, less bulky and more comfortable device that collects the small amounts of urine discharged between normal voiding.

Therefore, a need remains for a device that collects small amounts of urine leaked or discharged from incontinent males that does not necessarily occlude the leakage of urine and is not highly cumbersome to the user.

SUMMARY

The present disclosure relates to devices for management of male urinary incontinence, particularly for collecting small amounts of urine discharged between normal voiding. The present disclosure further relates to methods associated with the devices, including methods of use and manufacture. In one aspect of the present disclosure, the devices include male external urinary catheters that have an absorbent suitable for absorbing the small amounts of urine discharged between normal voiding.

A variety of examples of desirable device features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

BRIEF DESCRIPTION OF THE DRAWINGS

FIG. 15 is a side view of a mandrel used to form the tubular sheath of the external urinary catheter of the present invention;

FIG. 16 is a partial cross-sectional view of the mandrel of FIG. 15 shown when partially coated with a silicone coating;

FIG. 17 is a view similar to FIG. 16, but after the mandrel is partially coated with an adhesive layer;

FIG. 18 is a view similar to FIG. 17, but after a portion of the silicone coating and the adhesive layer on the mandrel have been stripped away;

FIG. 19 is a view similar to FIG. 18, but after a first overcoat layer of silicone rubber solution has been coated on the mandrel over the adhesive layer and silicone coating remaining on the mandrel;

FIG. 20 is a view similar to FIG. 19, but after an application of a second overcoat layer of a silicone rubber solution to a portion of the mandrel;

FIG. 21 is a view similar to FIG. 20, but after a step of curing or vulcanizing the tubular sheath, and showing an upper portion of the tubular sheath of the external urinary catheter rolled up;

FIG. 24 is a top plan view of yet another embodiment of an external urinary catheter of the present invention; and FIG. 25 is a side view of a portion of the external urinary catheter of FIG. 24.

DETAILED DESCRIPTION OF THE PREFERRED EMBODIMENT

Reference will now be made in detail to various features of the present disclosure that are illustrated in the accompanying drawings. Wherever possible, the same reference numbers will be used throughout the drawings to refer to the same or like parts.

I. Structural Description, Generally

Figure 1:
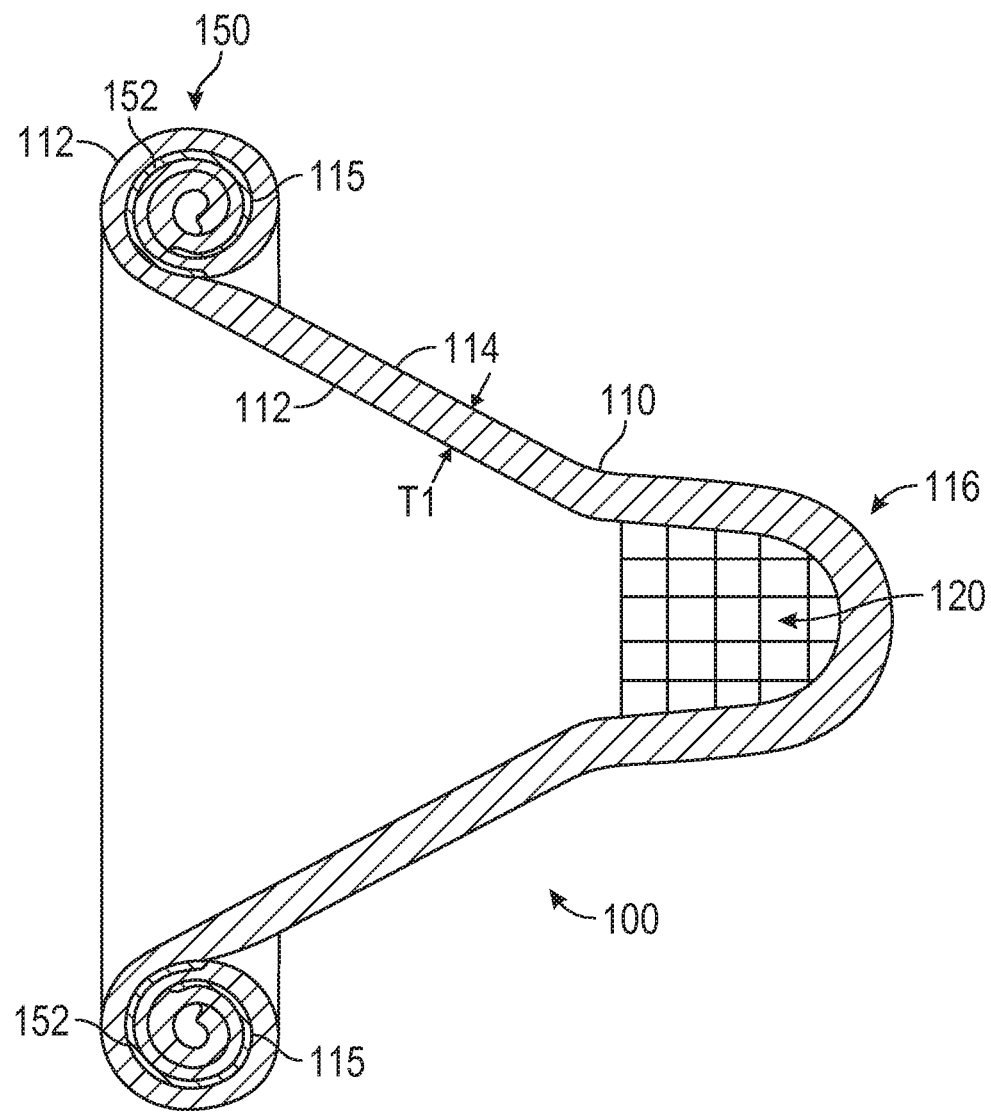
FIG. 1 is an enlarged cross sectional view of an external urinary catheter of the present invention shown in a pre-use orientation.

Referring to FIG. 1, one embodiment of an external urinary catheter 100 is illustrated. The external urinary catheter 100 generally includes a tubular sheath 110, an adhesive layer 115, and absorbent material 120.

Following manufacture and during pre-use storage, the external urinary catheter 100 will generally have a pre-use orientation, as shown in FIG. 1. In the pre-use orientation, an upper portion 150 of the tubular sheath 110 is rolled up as shown. The tubular sheath 110 of the catheter 100 has an inner surface 112 and an outer surface 114. When the upper portion 150 is rolled up in the pre-use orientation, the inner surface 112 contacts the outer surface 114 of the tubular sheath 110.

The adhesive layer 115 of the external urinary catheter 100 is provided on the inner surface 112 of the tubular sheath 110 during manufacture. Typically, the adhesive layer 115 includes a biocompatible adhesive. A biocompatible adhesive is an adhesive that can contact skin for extended periods without irritating or damaging the skin. Typically, the adhesive layer 115 is non-releasably bonded to a bonding region 152 of the inner surface 112, as will discussed in greater detail hereinafter. "Non-releasably bonded", "non-releasable adherence", or "non-releasable contact" refers to contact that does not permit easy separation of the adhesive layer 115 from the bonding region 152 of the tubular sheath 110.

When the external urinary catheter 100 is in a pre-use orientation, the adhesive layer 115 is non-releasably bonded to the bonding region 152 of the inner surface 112, and releasably bonded to the outer surface 114 of the tubular sheath 110. "Releasably bonded", "releasable adherence", or "releasable contact" refers to contact that permits a relatively easy separation of the adhesive layer 115 from the outer surface 114 of the tubular sheath 110. The adhesive layer 115 releases and separates from the outer surface 114 of the tubular sheath 110 when the upper portion 150 of the sheath 110 is unrolled, while the adhesive layer 115 remains non-releasably adhered to the bonding region 152 of the tubular sheath 110.

Still referring to FIG. 1, the absorbent material 120 of the external urinary catheter generally functions to absorb leaked or discharged urine. As will be described in greater detail hereinafter, the absorbent material 120 can either be attached to tubular sheath 110 or simply contained within the tubular sheath 110. In embodiments that simply contain the absorbent material 120, it is contemplated that the absorbent material can be replaced or exchanged by the user without utilizing a different tubular sheath 110.

General examples of suitable absorbent material include, but are not limited to: cotton fiber, cellulose fiber, absorbent polymers, hydrophilic absorbing power (powders having a chemical structure that hold moisture either inter-molecularly or intra-molecularly), synthetic fibers, and other types of material that absorb urine.

More specific examples of cellulose fibers include wood pulp, stabilized wood pulp, wood pulp with super absorbent, peat moss board, tissue paper, or creped wadding. More specific examples of synthetic fibers include nonwoven fibers of polypropylene, polyester, nylon, polyethylene, and copolymers thereof. One example of a suitable synthetic fiber is isotactic polypropylene.

More specific examples of absorbent polymers include polypropylene, polyacrylates such as sodium polyacrylate, and copolymers thereof. Absorbent polymers formed as a foam material can also be used. Such foam materials can be formed from the water actuation of polymers based on either toluene diisocyanate (TDI) or methylene diphenyl diisocyanate (MDI), for example. Theses polymers are commercially available under, for example, the trademarks "HYPOL" (TDI) and "HYPOL PLUS" (MDI) from W.R. Grace & Co., Organic Chemicals Division (Lexington, Mass.). Polymer foams can also be formed from polyurethanes or polyolefins.

The external urinary catheter 100 of the present disclosure may include various volumes or amounts of the absorbent material 120. Generally speaking, the amount of absorbent material 120 used can be described by an actual volume of the absorbent, or by the volume of urine absorbed by the material. The amount of absorbent material 120 included depends on the type of the absorbent material and the level of urinary discharge for which the catheter 100 is designed. For example, the amount of absorbent material 120 used for men that have higher levels of urinary discharge will be greater than the amount used for men that have lower levels of urinary discharge.

In general, the absorbent material 120 functions to absorb urine collected in the tubular sheath 110. In the embodiment shown in FIG. 1, the absorbent material 120 is generally located in a distal end 116 of the tubular sheath 110. There are a number of different configurations of the tubular sheaths 110 in which absorbent material 120 can be generally located in the distal end 116. Examples of such alternative embodiments are shown in FIGS. 2-5.

Referring now to FIGS. 2-5, the distal end 116 of each of the tubular sheaths 110 has a different configuration. The different configurations of FIGS. 2-5 are only exemplary configurations; and other configurations are contemplated.

Figure 2:
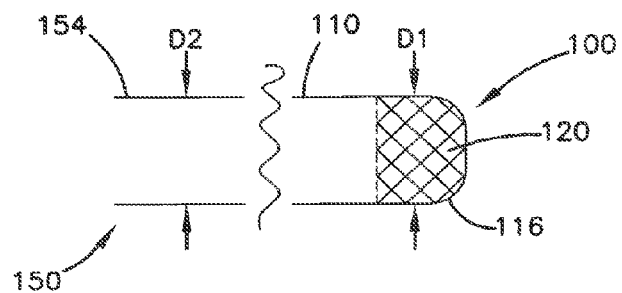
FIGS. 2 through 5 are cross sectional views of embodiments of the invention that have absorbent material in a distal end of the external urinary catheter.

Referring specifically to FIG. 2, the distal end 116 of the tubular sheath 110 has a generally square shape with a cross-sectional dimension D1. The cross-sectional dimension D1 is approximately equal to a diameter D2 of a main portion 154 of the tubular sheath 110. In an alternative embodiment, the cross-sectional dimension D1 can be larger or smaller than the diameter D2 of the remainder of the tubular sheath 110.

Figure 3:
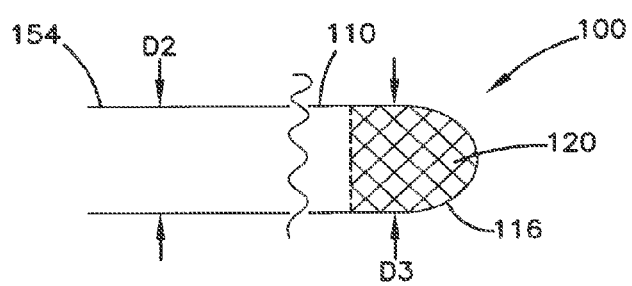
Figure 4:
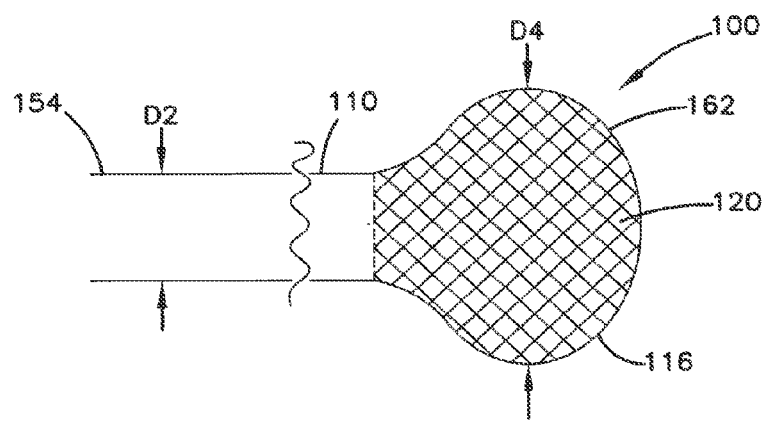

In FIG. 3, the distal end 116 of the tubular sheath 110 has a generally rounded shape with a maximum diameter D3. The maximum diameter D3 is approximately the same as that of the main portion 154 of the tubular sheath 110. In FIG. 4, the distal end 116 has a generally round shape with a maximum diameter D4. The maximum diameter D4 is greater than that of the main portion 154 of the tubular sheath 110.

Figure 5:
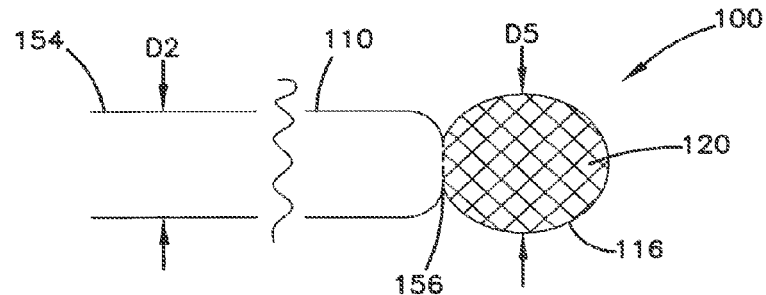

In FIG. 5, the distal end 116 has a generally round shape with a maximum diameter D5 that is also greater than the diameter D2 of the main portion 154 of the tubular sheath 110. However, in FIG. 5, the distal end 116 includes a necked portion 156 that reduces in diameter prior to expanding to the maximum diameter D5. In an alternative embodiment, the tubular sheath 110 can include a necked portion that expands to a maximum diameter D5 that is less than the diameter D2 of the main portion 154. It should also be understood that any combinations of these and other distal end constructions and shapes could be utilized. For example, the distal end 116 can have a necked portion, and include a generally square shape with a dimension greater than or less than the main portion 154 of the tubular sheath 110.

Figure 6:
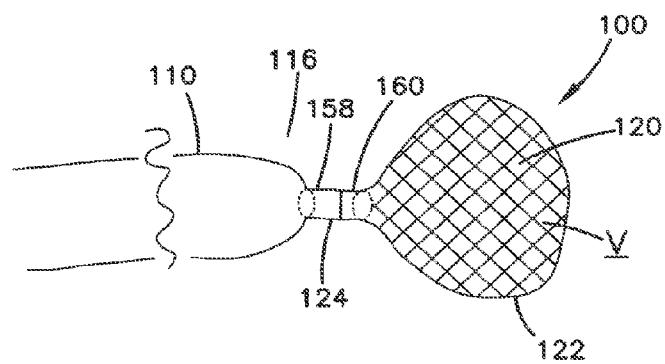
FIGS. 6 through 8 are cross sectional views of embodiments of the invention that have absorbent material in a reversibly joined receptacle of the external urinary catheter.
Figure 7:
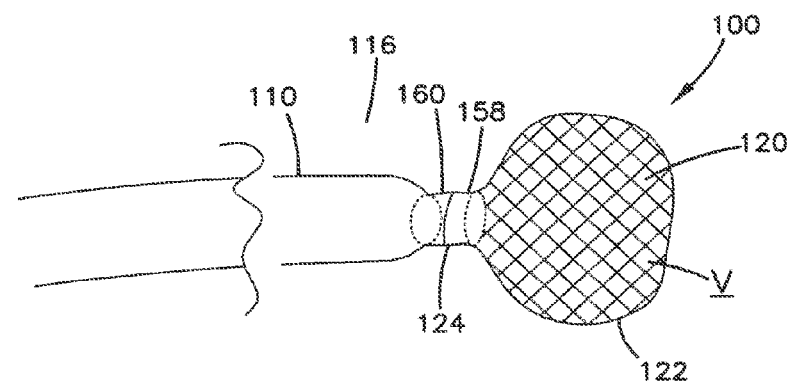
Figure 8:
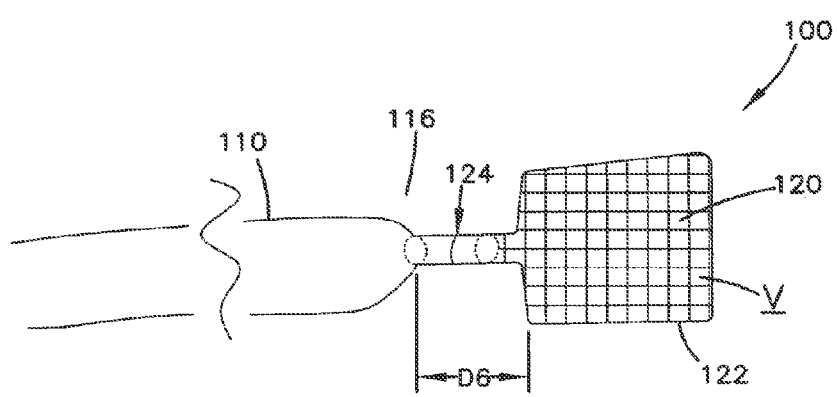

Referring now to FIGS. 6-8, in alternative embodiments, the absorbent material 120 can be located in a receptacle 122 (e.g. a pouch or cartridge). (See also FIG. 24.) Typically, the receptacle 122 is interconnected to the distal end 116 of the tubular sheath 110 by a joining assembly 124.

The receptacle 122 can be fashioned from a material that is one or more of pliable, durable, collapsible, and inexpensive. For example, the receptacle 122 can be pliable so that the catheter 100 is more malleable and comfortable for a user.

The receptacle 122 can be durable to limit the possibility of the receptacle 122 being pierced or ruptured. The receptacle 122 can be inexpensive so that the receptacle 122 can be replaced whenever appropriate without excessive cost. Examples of suitable materials that can be used to manufacture the receptacle 122 include, for example, polyvinyl chloride (PVC), polyurethane, block copolymers such as kraton, high density polyethylene, low density polyethylene, and silicone rubber. As can be understood, the receptacle 122 is in certain embodiments waterproof (i.e., not permeable to water over the length of time that the receptacle will remain in the user's undergarment). The material can have a waterproof quality, or a waterproofing material can be applied during the manufacture of the receptacle 122.

Generally, the thickness of receptacle 122 (i.e., the dimension that would be shown in a side view of FIG. 6-8) varies depending on the type of material used, and the type and amount of absorbent material 120 used. Typically, the thickness of receptacle 122, including the absorbent material 120, ranges from about 0.125 inches to about 1.50 inches; more typically between about 0.125 inches and 0.750 inches. Preferably, the thickness of the receptacle 122 is sized to be comfortable and concealable.

The capacity of the receptacle 122 varies depending on the level of urinary discharge for which the specific embodiment is designed. Embodiments designed for higher levels of urinary discharge will have receptacles 122 with a higher capacity, while those designed for lower levels of urinary discharge will have receptacles 122 with a lower capacity. The capacity of the receptacles 122 can be smaller than a leg bag and suitable for receiving discharge between voiding. Typically, the receptacle 122 has a capacity or volume V from about 25 mL to about 100 mL. Generally speaking, if the receptacle 122 is designed for higher levels of urinary discharge, the receptacle has a volume V of about 40 to 100 mL. If the receptacle 122 is designed for lower levels of urinary discharge, the receptacle has a volume V of about 25 to 35 mL.

The shape of receptacle 122 can vary. Exemplary configurations of the receptacle 122 are illustrated in FIGS. 6-8. As shown, the receptacle 122 can have virtually any shape, including a generally round shape (FIGS. 6 and 7) and a generally square shape (FIG. 8).

Embodiments that include the receptacle 122 can be designed so that receptacles of variable capacity can be used interchangeably. This feature allows a user to vary the capacity of the external urinary catheter 100 based on a personal level of urinary discharge, which may or may not vary. For example, in one embodiment, a kit may be provided to a user. The kit may include a tubular sheath 110 along with an array of receptacles 122. Each receptacle provided would include a different amount of absorbent material contained within the receptacle. This would permit the user to adjust the capacity of the external urinary catheter 100 according to the daily needs of the user.

In use, discharged urine flows from the sheath 110, through the joining assembly 124, and into the receptacle 122. The joining assembly 124 of the external urinary catheter 100 functions to reversibly join the receptacle 122 to the distal end 116 of the tubular sheath 110. What is meant by "reversibly join" is that the receptacle 112 sealingly attaches to the tubular sheath 110, yet is detachable or removable from the sheath without causing damage to the sheath.

The joining assembly 124 is sized and constructed such that the receptacle 122 is located a distance near the distal end 116 of the tubular sheath 110, as opposed to a leg bag which is located a distance away from the tubular sheath 110. Typically, the receptacle 122 is located in relation to the tubular sheath 110 such that the entire catheter 100, including the receptacle 122, is located at and within the pelvic region of the user. That is, the tubular sheath 110, the joining assembly 124, and the receptacle 122 can all fit within a user's undergarment at the urinary area. The user is thereby not encumbered with routing tubes through the undergarment to locations away from the urinary area, such as is required by conventional leg bags, for example. In the illustrated embodiment, the receptacle 122 is located a distance D6 (e.g. FIG. 8) of about one inch to about three inches from the distal end 116 of the tubular sheath 110.

In the embodiment of FIG. 6, the joining assembly 124 includes a female connector 158 extending from the distal end 116 of the tubular sheath 110, and a male connector 160 extending from the receptacle 122. In the embodiment of FIG. 7, the female connector 158 of the joining assembly 124 extends from the receptacle 122, and the male connector 160 extends from the distal end 116 of the tubular sheath 110. In each embodiment, the male connector 160 fits within the female connector 158 so that the tubular sheath 110 is reversibly joined to the receptacle 122.

In another embodiment, the joining assembly 124 can include a lock and unlock feature so that receptacle 122 is more securely reversibly joined to tubular sheath 110. In yet another embodiment, the joining assembly 124 functions like or includes a luer lock type assembly. As shown in FIGS. 6-8, the size of joining assembly 124 can vary. For example, in FIG. 7, the joining assembly 124 is larger than the joining assemblies shown in FIGS. 6 and 8. In an embodiment, the joining assembly 124 is large enough so that urine flow into the receptacle 122 is not restricted.

Referring now to FIGS. 24 and 25, another alternative embodiment of the external urinary catheter 100 is illustrated. Similar to some of the previous embodiments, the tubular sheath 110 of this embodiment is interconnected to the receptacle 122 via the joining assembly 124.

As shown in FIG. 24, the distal end 116 of the tubular sheath 110 defines an opening 166 that receives the joining assembly 124. The joining assembly 124 provides fluid communication between the tubular sheath 110 and the receptacle 122. The opening 166 is located in the tapering or necked portion 156 of the tubular sheath.

The joining assembly 124 in the illustrated embodiment includes a hollow fitting 130 and a tube member 140. In an embodiment, each of the hollow fitting 130 and the tube member 140 of the joining assembly 124 is sized so that urine flow into the receptacle 122 is not restricted.

The hollow fitting 130 has first and second ends 132, 134. Each of the first and second ends 132, 134 is a male fitting end. The first male fitting end 132 is sized and constructed for receipt within the opening 166 formed in the distal end 116 of the tubular sheath 110. In the illustrated embodiment, the first male fitting end 132 includes ridges 138 that taper to ease insertion and removal of the fitting 130 into and from the opening 166. Other embodiments may include a first end 132 that continuously tapers without ridges, or that has a straight fitting construction.

The second male fitting end 134 is received within a first end 142 of the tube member 140. In the illustrated embodiment, the second male fitting end 134 is secured within the first end 142 of the tube member 140 by an adhesive or other securing material or construction. In the illustrated embodiment, the second male fitting end 134 is a straight fitting end. Other embodiments may include a second end 134 that continuously tapers or includes ridges.

A second end 144 of the tube member is positioned within an opening 90 formed in the receptacle. In the illustrated embodiment, the second end 144 of the tube member 140 is secured within the opening 90 of the receptacle 122 by an adhesive or other securing material or construction.

In the embodiment shown in FIGS. 24 and 25, the receptacle 122 is constructed from a material that is pliable and durable, such as PVC, for example. In particular, first and second sheets or plies 168, 170 of the material are joined together to form an interior 172 for receipt of the absorbent material 120. In one embodiment, the two plies may be sewn together along a seam 102, or adhered together along the seam. The PVC receptacle 122 also has sufficient pliability so that the catheter 100 is more malleable and more comfortable for a user. In addition, the PVC receptacle 122 is durable to limit the possibility of the receptacle 122 being pierced or ruptured. Further, the PVC receptacle has moisture impermeable qualities that contain moisture absorbed by the absorbent material 120 within the interior 172 of the receptacle 122 so that the exterior of the receptacle 122 remains dry.

As shown in FIGS. 24 and 25, the receptacle 122 generally has a width W, a height H, and a thickness T, although the disclosed principles can be applied in a variety of sizes and applications. The width W of the receptacle 122 can be, for example, between 1.5 and 5.0 inches or between about 2.0 and 3.0 inches. The height H of the receptacle 122 can be, for example, between 2.0 inches and 6.0 inches or between about 3.0 and 4.0 inches. The thickness T of the receptacle 122 is generally between 0.125 inches and 1.50 inches, depending upon the type of absorbent material 120 used. In an embodiment, the thickness T is between about 0.5 and 1.0 inches. Further, the distance D6 (see FIG. 6) between the receptacle 122 and the distal end 116 of the tubular sheath 110 when assembled (not shown) can be between 2.0 inches and 6.0 inches; e.g., between about 3.5 and 4.5 inches.

Each of the width W, the height H, the thickness T, and the distance D6 are sized and dimensioned such that the receptacle 122 conveniently fits within the undergarment of the user. That is, the receptacle 122 is sized so that the entire catheter 100 fits within the user's underwear, and does not required that the receptacle be attached or located at a location away from the pelvic area of the user. Accordingly, the PVC material of the receptacle 122 is also chosen to be comfortable against the user's skin. For example, the exterior of the receptacle 122 can be flocked with cotton or synthetic flocking, or embossed. As previously discussed, the shape of receptacle 122 can vary. In the embodiment of FIGS. 24 and 25, the receptacle 122 has a rectangular configuration, although any shape that comfortably fits an average-sized male can be used.

At the same time, the receptacle 122 is sized to provide a urine absorbing capacity depending on the level of urinary discharge between normal voiding. As previously described in relation to the other embodiments, the capacity of the receptacle 122 of FIG. 24 can be smaller than a leg bag and suitable for receiving discharge between voiding. The width W, height H, and thickness T of the receptacle 122 defines a volume associated with the receptacle 122. The capacity of the receptacle 122 is a function of the volume and the type of absorbent material 120 used. In an embodiment, the volume of the receptacle 122 is between 1.0 cubic inch and 5.0 cubic inches. In one embodiment, the absorbent material 120 is cellulose fiber. In providing cellulose fiber absorbent material in the volume of between about 3.0 and 4.0 cubic inches, the receptacle 122 has a capacity to contain between about 45 and 60 mL of urine. Because the receptacle 122 is sized to fit within the user's pelvic region, (i.e., within the user's undergarment) the capacity of the receptacle 122 is typically no more than about 100.0 mL.

Similar to the previous embodiments, the embodiment of FIG. 24 is designed so that the receptacle 122 can be interchanged. This feature allows a user to vary the capacity of the external urinary catheter 100 based on a personal level of urinary discharge, which may or may not vary. For example, a user may interchange a first receptacle with a second receptacle having a different amount of absorbent material or a different type of absorbent material to adjust the capacity of the external urinary catheter 100.

The receptacle 122 is also interchangeable so that a user can replace a filled or used receptacle with a new receptacle as needed. For example, during use of the catheter 100 embodiment of FIG. 24, urine discharged into the sheath 110 flows through the joining assembly 124 and into the receptacle 122. When the receptacle 122 has filled, the user detaches the filled receptacle by removing the first end 132 of the fitting 130 from the opening 166 in the tubular sheath 110. The tubular sheath 110 remains in position on the penis. A new receptacle is then attached to the distal end 116 of the tubular sheath.

The joining assembly 124 of the external urinary catheter 100 functions to reversibly join the receptacle 122 to the distal end 116 of the tubular sheath 110. In the embodiment of FIG. 24, the joining assembly 124 attaches and detaches from the tubular sheath 110 (i.e., the joining assembly 124 is removed or detached along with the receptacle 122). In an alternative embodiment, the catheter 100 can be constructed such that the receptacle 122 attaches and detaches from the joining assembly 124 (i.e., only the receptacle 122 is removed or detached).

The receptacle 122 can also be disposable. The user may simply throw away the receptacle when the receptacle has been filled. In alternative embodiments, the receptacle 122 may be recycled. That is, the receptacle can be configured to provide access to the absorbent material 120 so that used absorbent material can be removed and replaced with new material, and the receptacle 122 reused.

Various alternative embodiments including other features can be practiced in accord with the principles disclosed. For example, the external urinary catheter 100 may include more than one type of absorbent material 120. For instance, a synthetic fiber such as polypropylene, polyester, nylon, polyethylene, or copolymers thereof can be spunbound to create a coverstock for another absorbent. A coverstock functions to provide a semi-permeable membrane or barrier that allows moisture to pass through that barrier so that the moisture is absorbed by another absorbent material enclosed within the barrier. Use of a coverstock provides a number of advantages, including keeping the skin of the user more dry, and retaining the absorbent material 102 in a particular location, such as a distal end 116 of the tubular sheath 110. Suitable examples of synthetic fibers that can be spunbound to form coverstock include polyester and polypropylene.

Figure 9:
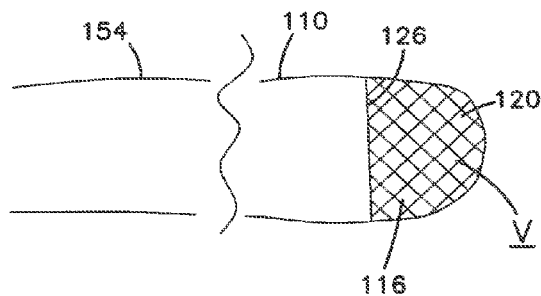
FIGS. 9 and 10 are cross sectional views of embodiments of the invention that also include a semi-permeable barrier.
Figure 10:
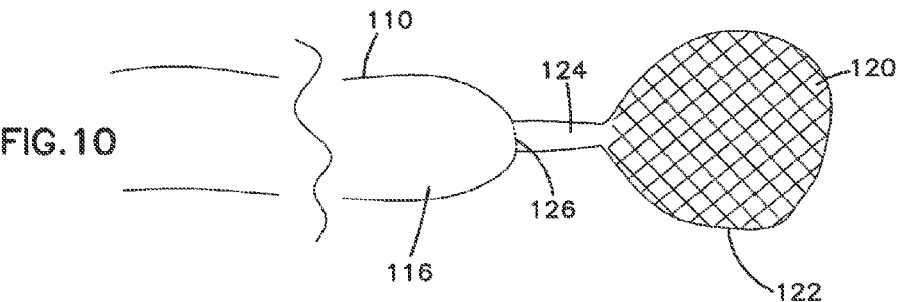

Referring now to the external urinary catheters 100 of FIGS. 9 and 10, two embodiments of a coverstock or semi-permeable barrier 126 are illustrated. In the embodiment of FIG. 9, the semi-permeable barrier 126 is located adjacent to the distal end 116 of the tubular sheath 110. In the embodiment of FIG. 10, the semi-permeable barrier 126 is in the joining assembly 124.

Figure 13:
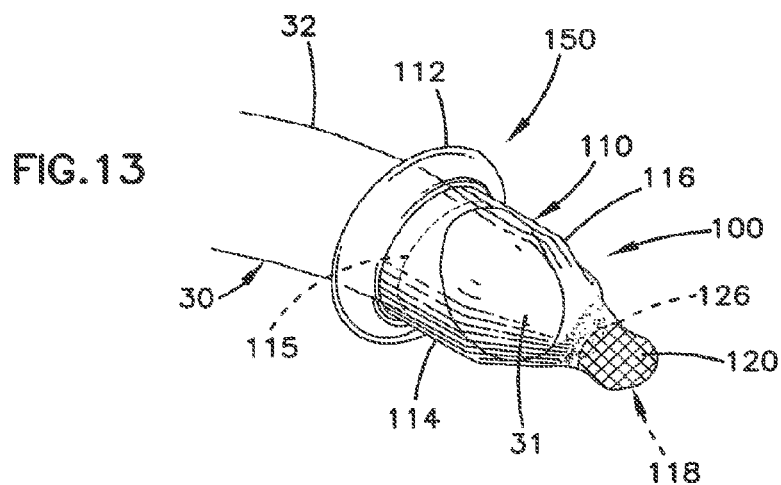
FIG. 13 is a perspective view of the external urinary catheter of FIG. 1 shown when the catheter is partially unrolled onto a penis.
Figure 14:
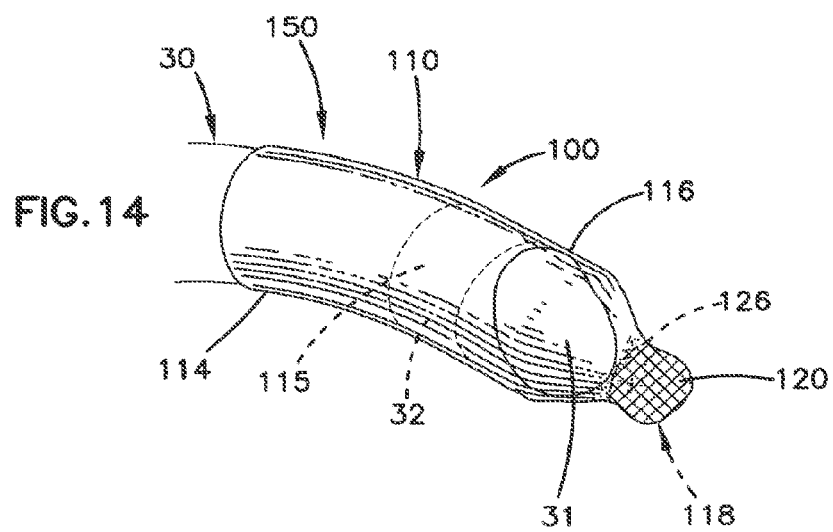
FIG. 14 is a perspective view of the external urinary catheter of FIG. 13 shown when the catheter is fully unrolled onto the penis.

The semi-permeable barrier 126 functions to allow urine to pass into the absorbent material 120, but does not allow the absorbent material 120 to migrate through to the main portion 154 of the tubular sheath 110. Alternatively, or in addition, the semi-permeable barrier 126 can function to allow urine to pass through into the volume V containing the absorbent material 120, but does not allow urine to pass out of the volume V. In an embodiments in which the absorbent material 120 is completely contained or surrounded by the barrier 126, the barrier 126 and the absorbent material 120 can be replaced or exchanged by the user without utilizing another tubular sheath 110. For example, as shown in FIGS. 13 and 14, the barrier 126 and absorbent material 120 can be provided in the form of a packet 118. The packet 118 can be replaced and exchanged without utilizing another tubular sheath 110. It is to be understood that the semi-permeable barrier can be incorporated into any of the embodiments shown, and in combination with any other features described.

Figure 11:
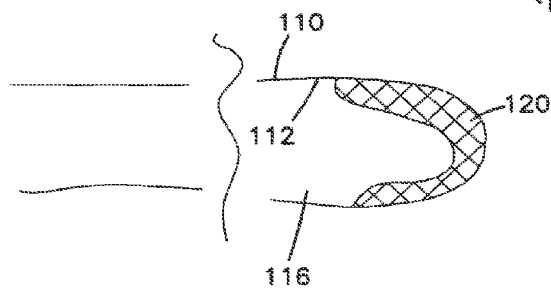
FIG. 11 is a cross sectional view of an embodiment of the invention that has the absorbent material adhered to an inner surface of a tubular sheath.
Figure 12:
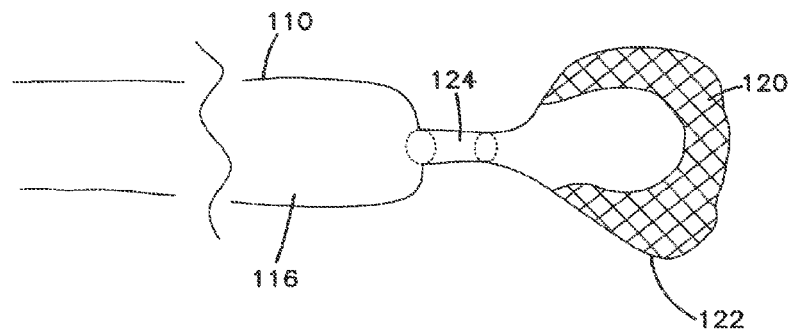
FIG. 12 is a cross sectional view of an embodiment of the invention that has the absorbent material adhered to the inner surface of the receptacle.

Another alternative embodiment including another feature that can be practiced in accord with the principles disclosed is illustrated in FIG. 11. In this embodiment the absorbent material 120 of the external urinary catheter 100 is adhered to the inner surface 112 of the tubular sheath 110. Adhering the absorbent material 120 to the inner surface 112 prevents the absorbent material 120 from migrating within the tubular sheath 110. Methods of adhering the absorbent material 120 to the inner surface 112 of the tubular sheath 110 vary depending on the composition of the absorbent material 120. The absorbent material 120 can also be adhered to the inner surface of the receptacle 122, as shown in FIG. 12. It is to be understood that adhering the material to an inner surface can be incorporated into any of the embodiments shown, and in combination with any other features described.

II. Method of Use

The external urinary catheter 100 is typically worn by users that discharge relatively small amounts of urine between normal voiding, as compared to users that discharge an amount that necessitates a leg bag. Referring to FIGS. 13 and 14, in use, a user, or perhaps a health care professional, engages a tip 31 of a penis 30 with the external urinary catheter 100 in the pre-use orientation (shown in FIG. 1). In particular, the distal end 116 of the tubular sheath 110 is applied to the tip 31 of the penis 30. The upper portion 150 of the tubular sheath 110 is then unrolled using moderate force to press the rolled up portion of the upper portion 150 in a direction away from the tip 31 of the penis 30. This can generally be accomplished by pressing on the rolled upper portion 150 with one's thumb and forefinger (not shown).

As the upper portion 150 unrolls, the adhesive layer 115 releases from the outer surface 114 of the tubular sheath 110. In an embodiment, the releasability characteristics are such that the upper portion 150 is relatively easy to unroll onto the penis 30. As the adhesive layer 115 comes into contact with an outer surface 32 of the penis 30, the adhesive layer 15 adheres to the outer surface 32. This secures the external urinary catheter 100 to the penis 30. In an embodiment, the adhesive layer 115 seals the tubular sheath 110 to the penis 30 such that leakage above the area where the adhesive layer 115 contacts the outer surface 32 of the penis 30 is prevented. The external urinary catheter 100 secures to the user only at the location where the adhesive layer 115 contacts the outer surface 32 of the penis. No other belts, straps, garments, or coupling/attaching devices are necessary. The catheter 100 of the present invention thereby provides a more comfortable solution to incontinence, and is not highly cumbersome or bulky for the user.

The external urinary catheter 100 can be removed from the penis 30 by pulling the upper portion 150 of the tubular sheath 110 away from the penis 30 and down over the outer surface 114. Removal can be accomplished in any manner that accommodates the comfort of the patient. It will be appreciated that one appropriate method of removing the catheter 100 is to roll the upper portion 150 up again so that the catheter 100 returns to generally the same orientation as that shown in FIG. 1. When removing the catheter 100, the adhesive layer 115 releases the outer surface of the penis 30, and the catheter 100 can be removed from the penis 30 with relative ease.

Generally speaking, the external urinary catheter 100 can be worn for variable amounts of time depending on the user, the capacity for which the device is designed, and the amount of urinary discharge the user is experiencing. For example, the external urinary catheter 100 can be worn for certain defined periods of time, until the catheter begins to feel uncomfortable, until the absorbent has reached an absorbance capacity, or until the user removes the catheter to void.

Depending on the specific absorbent material 120 utilized, the catheter 100 may exhibit altered characteristics when the material has absorbed an amount of urine. Examples of such altered characteristics include an increase in the weight of the catheter 100 and a change in the flexibility of the portion of the catheter 100 that contains the absorbent material 120. In certain embodiments, the absorbent material can change color to indicate that material is saturated with urine. Changes such as these and others can also be used by the wearer to determine when the catheter 100 should be removed and/or replaced.

In addition, in embodiments having a detachable receptacle 122 (e.g., FIG. 24), the tubular sheath 110 can be worn throughout the day, not only between voiding. In particular, the receptacle 122 can be detached when the user needs to void. The user can then void through the open end 166 of the tubular sheath 110, and then reattach the receptacle 122 or reattach a replacement receptacle to the same tubular sheath 110.

III. Method of Manufacturing

As described herein below, the tubular sheath 110 can be made by combining two or more layers of a silicone rubber solution or of separate silicone rubber solutions. Once the silicone rubber solutions are dried and cured in a vulcanizing process, the respective silicone rubber solution coatings combine to form a single unitary tubular sheath without separate layers. It will be appreciated that any silicone rubber solution used to form silicone rubber products of one type or another may be used to form the silicone rubber sheath of the present invention. The vulcanizing process may be either a heat process, a catalyzed process employing a catalyzing agent or agents, a combination of the two, or any other suitable vulcanizing process known in the art.

Referring now to FIGS. 15-22, a suitable method of making an external urinary catheter 100 of the present invention includes a series of steps designed to coat a mandrel 20. The mandrel 20 has a generally cylindrical shape, which may narrow or taper at a lower end 22 (FIG. 15). In one embodiment, the lower end 22 of mandrel 20 may include a larger diameter than that of the remaining mandrel 20. The mandrel 20 having a larger lower end diameter may be utilized to form a bulbous portion 162 at the distal end 116 of the tubular sheath 110, such as shown in FIG. 4. Alternatively, the lower end 22 of mandrel 20 may be configured to provide the embodiments shown in FIGS. 2, 3, and 5. In certain embodiments, either the external surfaces 164 of the mandrel 20 are coated with Teflon®, or the mandrel 20 is made of Teflon®. A tip (not shown) for forming male or female connectors 158, 160 (FIGS. 6 and 7) of the joining assembly 124 can be coupled to the lower end 22 of the mandrel 20.

Figure 22:
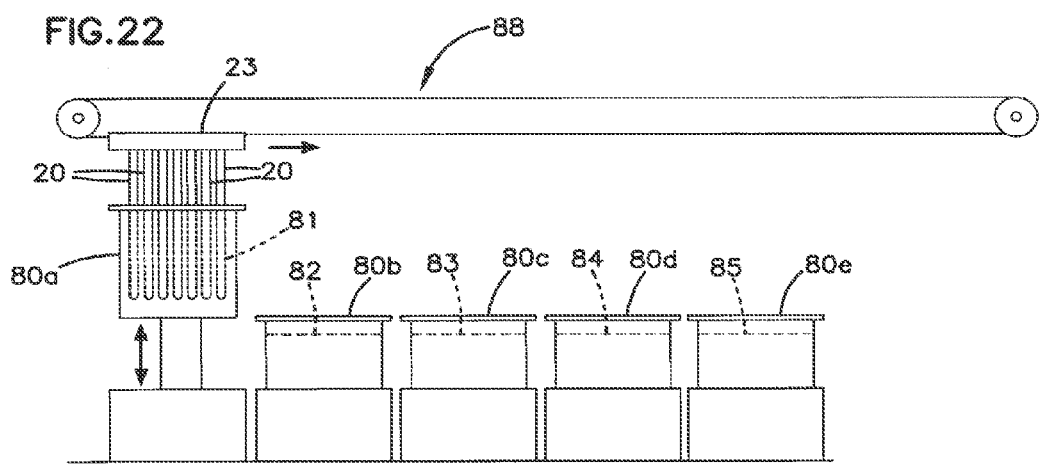
FIG. 22 is a schematic illustration of a mechanized system used to coat the mandrels, as shown in FIGS. 15-21.

In an embodiment, depicted in FIG. 22, a series of mandrels 20 are attached to a pallet 23 so that numerous external urinary catheters 100 can be mass-produced. This can be accomplished by coating each of the mandrels 20 in a series of coating steps. The coating steps include dipping each of the mandrels 20, e.g., in unison, in a series of dip tanks 80a-e that are raised up to a precise level calculated to accomplish a specific task. It will be appreciated that a series (not shown) of pallets can also be employed so that a continuous mechanized production operation can be developed to mass-produce catheters 100. The pallet 23 or a series of pallets (not shown) are advanced by a mechanized advancing system 88. It will be appreciated that any known mechanization system for advancing the pallet 23 or pallets can be used.

Referring now to FIGS. 16 and 22, in one method of manufacture, a first portion 24 of the mandrel 20 is coated with a silicone coating 40. The first portion 24 of the mandrel 20 is defined as the area of the mandrel between dashed lines A and B illustrated in FIG. 16. To create the silicone coating 40, the pallet 23 of mandrels 20 is dipped into a first dip tank 80*a* containing a fluid silicone release agent 81, e.g., a polydimethylsiloxane fluid (Dow Corning 360 Medical Fluid from Dow Corning, Inc., Midland, Mich. 48360) having a viscosity of 12,500 centistokes, diluted about 1:25 in hexamethyldisiloxane. The fluid silicone release agent 81 forms the silicone coating 40. In order to ensure that the first portion 24 (FIGS. 16-18) of the mandrel 20 is completely coated with the silicone coating 40, the pallet 23 to which the mandrels 20 are attached is centered over the first dip tank 80*a* and the dip tank 80*a* is raised a calculated distance, as shown. The distance is calculated such that the mandrel 20 is submersed within the release agent 81 to a designated level corresponding to the dashed line A. At the designated level, the entire first portion 24 of mandrel 20 is submersed. After the first portion 24 is fully submersed, the first dip tank 80*a* is lowered and the silicone coating 40 is permitted to dry (FIG. 16).

Referring now to FIGS. 17 and 22, the pallet 23 is then advanced to a second dip tank 80*b* containing adhesive material or fluid 82. The adhesive material 82 bonds to unvulcanized silicone rubber during a vulcanizing process. The adhesive material 82 can include a suitable polymeric adhesive, such as a suitable copolymer of acrylic acid esters with vinylacetate, or cross linking pressure sensitive adhesive, for instance. One example of an adhesive that can be used is Gelva MAS 788 manufacture by Solutia Inc. (St. Louis Mo.). The second dip tank 80*b* is raised a distance (not shown) calculated to dip the mandrel 20 into the adhesive fluid 84 in the second dip tank 80*b* so that the entire first portion 24 of the mandrel 20 between the lines designated A and B is coated by the adhesive fluid 82. As shown in FIG. 17, the adhesive fluid 82 forms the adhesive layer 115, which is disposed over the silicone coating 40. The second dip tank 80*b* is then lowered, and the adhesive layer 115 allowed to dry for a period of time.

Referring now to FIGS. 18 and 22, the pallet 23 is then advanced to a third dip tank 80*c* containing a solvent 83, e.g., trichloroethane (trichlor 1,1,1) or xylene. The solvent 83 strips or removes the adhesive layer 115 and the silicone coating 40 from the mandrel 20. In this step, the dip tank 80*c* is raised a distance (not shown) calculated to dip the mandrel 20 into the solvent 83 up to the line on the mandrel 20 designated B so that the adhesive layer 115 and the silicone fluid coating 40 which coat a second portion 26 of the mandrel 20 is stripped. The second portion 26 of the mandrel 20 is defined as the area of the mandrel below the line designated B, and proximate the lower end 22 of the mandrel 20. In some methods, the tank 80*c* may be lowered and raised several times to provide a rapid stripping action. The pallet 23 can also be advanced to a new dip tank (not shown) having a second solvent (not shown) to further assist in stripping the second portion 26 of the mandrel 20. In some embodiments, a vibrator (not shown) is connected to the pallet 23 or the mandrel 20 to vibrate the mandrel 20 and speed the removal of the adhesive coating 115. In other embodiments, an ultrasonic cleaning system (not shown) is incorporated into the dip tank 80*c*.

In some methods, a further step can be added at this point in the manufacturing process. This step involves shaping the lower end 22 of mandrel 20 by selectively coating the lower end 22 with an agent that buildups the lower end 22. Shaping the lower end 22 of the mandrel 20 provides the shaped distal end 116 configurations of the catheter 100 previously disclosed. The agent can be the same or similar to that of the mandrel release agent 81 utilized previously.

In continuing the manufacture of the catheter 100, the mandrel 20 is advanced on the pallet 23 to a fourth dip tank 80*d* containing an unvulcanized silicone rubber solution 84 which can be a disiloxane solvent, e.g., a hexamethyldisiloxane solvent. The disiloxane solvent is suitable because the disiloxane solvent does not destroy the integrity of the adhesive layer 1715 that remains on the first portion 24 of the mandrel 20. When the mandrel 20 is dipped into the silicone rubber solution 84 in the fourth dip tank 80*d*, the silicone rubber solution 84 coats the mandrel 20 and overcoats the silicone coating 40 and the adhesive layer 115. This overcoating forms a first overcoat layer 46 as shown in FIG. 19. If the shaping step was performed, the first overcoat layer 46 will have a shaped region, such as an enlarged region, that eventually becomes the distal end 116 of the tubular sheath 110. The fourth dip tank 80*d* is then lowered, and the overcoat layer 46 is allowed to dry for a period of time.

Referring now to FIGS. 20 and 22, the pallet 23 is then advanced to a fifth dip tank 80*e* containing an additional silicone rubber solution 88. The additional silicone rubber solution 88 can have a greater concentration of silicone rubber than the first overcoat layer 46. The solvent may also be varied. The dip tank 80*e* is raised and the mandrel 20 is dipped into the dip tank 80*e* to a level just below the line designated B so as to add an additional thickness proximate the lower end 22 of the mandrel 20. This forms a final overcoat layer 48 over the first overcoat layer 46. The dip tank 80*e* is then lowered and the final overcoat layer 48 is allowed to air dry so that the solvent in the silicone rubber overcoat layer 46 evaporates. It will be appreciated that additional dip tanks may be provided for additional dipping steps.

In one embodiment, the first overcoat layer 46 has a generally uniform thickness through out the construction of the sheath 110. The thickness is typically between about 0.002 and 0.010 inches; e.g., between about 0.003 and 0.008 inches. The final overcoat layer 48 provides additional thickness in the proximal region 116 of the sheath 110. The thickness at the distal end 116 is between 0.020 to 0.080 inches; e.g., between about 0.030 to 0.060 inches.

In an embodiment of the method, the final overcoat layer 48 is vulcanized or cured in an oven (not shown) at an elevated temperature, e.g., about 205° F. It will be appreciated that the temperature is maintained at a level below the boiling point of the solvents of the silicone rubber solutions to prevent the formation of bubbles in the silicone rubber caused by evaporation or the boiling off of the solvents. Furthermore, it will also be appreciated that other silicone rubber systems that are catalyzed without heat may also be used to provide a vulcanizing system resulting in a vulcanized silicone rubber elastomeric construction 50.

Once the silicone rubber has been vulcanized, the tubular sheath 110 is formed. The tubular sheath 110 is permitted to cool. When cooled, the upper portion 150 of the tubular sheath is rolled from a top 25 of the mandrel 20 (FIG. 21) so that the inner surface 112 (FIG. 23) of the tubular sheath 110 rolls up onto the outer surface 114 of the tubular sheath. In the process of rolling the tubular sheath 110, the adhesive layer 115, which has now been integrally bonded with the silicone rubber during the vulcanizing process, comes into contact with the outer surface 114 of the tubular sheath 110.

Figure 23:
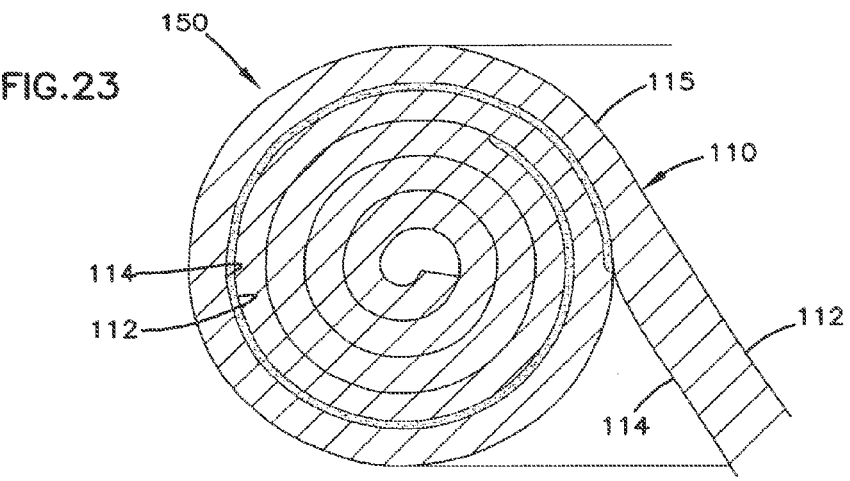
FIG. 23 is an enlarged cross-sectional view of the upper portion of the external urinary catheter of FIG. 1 in the pre-use orientation.

Referring to FIG. 23, when the catheter 100 is fully rolled up into its pre-use orientation (as shown in FIG. 1), the catheter 100 includes the single tubular sheath 110 (FIG. 1) having a unitary construction made of silicone rubber with an adhesive layer 115 integrally bonded to the tubular sheath 110. The adhesive layer 115 is interposed between the inner surface 112 and the outer surface 114 of the sheath 110. The adhesive layer 115 is integrally bonded to the inner surface 112 as a result of cross-linking between constituents in the adhesive layer 115 and constituents in the unvulcanized silicone rubber of the overcoat layer 46 during the vulcanizing process. The adhesive layer 115 will not, however, irreversibly adhere or bond to any of the vulcanized silicone rubber surfaces with which the adhesive contacts after the vulcanizing process. The adhesive layer 115 does contact the outer surface 114, but any adherence to the outer surface 114 is limited to releasable adherence.

In particular, when the upper portion 150 of the tubular sheath is rolled up, trace amounts of the silicone coating 40 adhere to the adhesive layer 115, and the remaining portion of the silicone coating 40 stays on the mandrel 20. The trace amounts of silicone coating 40 that adhere to the adhesive strip are absorbed by the outer surface 114 of the tubular sheath 110 when the coating 40 comes into contact with the outer surface 114.

It is to be appreciated that it is important that the trace amounts of silicone fluid adhering to the adhesive layer 115 are absorbed by the outer surface 114, because if not absorbed, the coating 40 could interfere with the adherence of the adhesive layer 115 with the penis 30. It will also be appreciated that the silicone coating 40 is just one of many mandrel release agents which can be used to coat the mandrel 20. Other agents that prevent making removal of the adhesive layer 115 from the mandrel 20 overly difficult can also be used.

The adhesive layer 115 is selected for its ability to bond with the silicone rubber during the vulcanized process and for its lack of adherence when the layer 115 comes into contact with vulcanized silicone rubber after the vulcanizing process. It will be appreciated that any biocompatible adhesive which will cross-link with silicone rubber during the vulcanizing process will be a suitable adhesive so long as the biocompatible adhesive will releasably adhere to new silicone rubber surfaces with which the biocompatible adhesive comes into contact after the adhesive is bonded to the inner surface of a silicone rubber sheath during the vulcanizing process.

Inclusion of the absorbent material 120 occurs after the above formation of the tubular sheath 110. The specific method of providing or including the absorbent material 120 depends on the specific type of the absorbent material 120 used, and the specific arrangement. For example, in the embodiments having the absorbent material 120 located in the distal end 116 of the sheath 110, the absorbent material 12 is typically placed at or adjacent to an enclosed tip 53 (FIG. 21) of the sheath 110. For instance, if the absorbent material 120 is hydrophilic powder, the material can simply be introduced into the tubular sheath 110, and directed towards the enclosed tip 53 at the distal end 116 of the sheath 110. If the hydrophilic powder is to be adhered to the inner surface 112 of the tubular sheath 110, a suitable adhesive, such as Gelva Mas 788, for example, can be applied to the desired portion of the tubular sheath 110 adjacent the enclosed tip 53 before the powder is introduced into the tubular sheath 110.

In the embodiments having the absorbent material 120 located in the receptacle 122, the enclosed tip 53 of the tubular sheath 110 is removed to provide the opening 166 (FIG. 24) at the distal end 116. The absorbent material 12 is disposed in the receptacle 122, and the receptacle is interconnected to the opening 166 at the distal end 116 via the joining assembly 124.

The above specification provides a complete description of the invention. Since many embodiments of the invention can be made without departing from the spirit and scope of the invention, certain aspects of the invention reside in the claims hereinafter appended.

We claim:

1. An external urinary catheter, comprising:
a tubular sheath including a closed distal end and an open proximal end;
a layer of adhesive material non-releasably bonded to a portion of an inner surface of the tubular sheath; and
an absorbent material positioned distal to the layer of adhesive material wherein the absorbent material is contained within and surrounded by a semi-permeable coverstock.

2. The external urinary catheter according to claim 1, wherein the tubular sheath is formed of silicone rubber.

3. The external urinary catheter according to claim 1, wherein the inner surface is rolled onto an outer surface of the tubular sheath in a storage configuration, the adhesive material releasably contacting the outer surface.

4. The external urinary catheter according to claim 1, wherein the distal end of the tubular sheath has an end dimension that is different than a diameter of the proximal end.

5. The external urinary catheter according to claim 1, wherein the distal end of the tubular sheath has an end dimension that is greater than a diameter of the proximal end.

6. The external urinary catheter according to claim 1, wherein the absorbent material is isolated from an adjacent section of the tubular sheath by a semi-permeable barrier.

7. The external urinary catheter according to claim 6, wherein the semi-permeable barrier comprises a spunbound synthetic fiber coverstock.

8. The external urinary catheter according to claim 1, wherein the coverstock is a spunbound synthetic fiber selected from the group consisting of polyester and polypropylene.

9. The external urinary catheter according to claim 1, wherein the absorbent material is positioned in the closed distal end of the tubular sheath.

10. The external urinary catheter according to claim 1, wherein the absorbent material includes cellulose fiber.

11. An external urinary catheter, comprising:
a tubular sheath including a closed distal end and an open proximal end;
a layer of adhesive material non-releasably bonded to a portion of an inner surface of the tubular sheath;
an absorbent material positioned distal to the layer of adhesive material; and
a receptacle detachably interconnected to the distal end of the tubular sheath, the receptacle defining an interior in which urinary discharge is collected, the absorbent material positioned in the receptacle, wherein the absorbent material is contained within and surrounded by a semi-permeable coverstock.

12. The external urinary catheter according to claim 11, wherein the receptacle is configured to reside within a user's pelvic region when the catheter is worn.

13. The external urinary catheter according to claim 11, further comprising a joining assembly positioned between the distal end of the tubular sheath and the receptacle, the joining assembly providing fluid communication between the tubular sheath and the receptacle.

14. The external urinary catheter according to claim 11, wherein the interior has a volume sized to collect no more than 50 mL of urine.

* * * * *